(12) United States Patent
Chen et al.

(10) Patent No.: US 7,854,923 B2
(45) Date of Patent: Dec. 21, 2010

(54) BIOPOLYMER SYSTEM FOR TISSUE SEALING

(75) Inventors: Weiliam Chen, Mount Sinai, NY (US); John M. Abrahams, Scarsdale, NY (US)

(73) Assignee: Endomedix, Inc., Newark, NJ (US)

( * ) Notice: Subject to any disclaimer, the term of this patent is extended or adjusted under 35 U.S.C. 154(b) by 227 days.

(21) Appl. No.: 11/530,362

(22) Filed: Sep. 8, 2006

(65) Prior Publication Data

US 2007/0243131 A1 Oct. 18, 2007

Related U.S. Application Data

(63) Continuation-in-part of application No. 11/379,182, filed on Apr. 18, 2006.

(51) Int. Cl.
*A61K 48/00* (2006.01)
*A61K 31/73* (2006.01)

(52) U.S. Cl. .......................... 424/70.27; 514/55; 514/2; 514/8

(58) Field of Classification Search ................ 424/422, 424/426, 488, 492, 70.27; 514/2, 8, 54–55; 264/4, 4.1
See application file for complete search history.

(56) References Cited

U.S. PATENT DOCUMENTS

| | | | |
|---|---|---|---|
| 3,879,376 A | 4/1975 | Vanlerberghe et al. | |
| 3,953,608 A | 4/1976 | Vanlerberghe et al. | |
| 4,454,110 A | 6/1984 | Caslavsky et al. | |
| 4,528,283 A | 7/1985 | Lang et al. | |
| 4,532,134 A | 7/1985 | Malette et al. | |
| 4,619,995 A | 10/1986 | Hayes | |
| 4,822,598 A | 4/1989 | Lang et al. | |
| 4,902,281 A | 2/1990 | Avoy | |
| 4,996,307 A | 2/1991 | Itoi et al. | |
| 5,093,319 A | 3/1992 | Higham et al. | |
| 5,607,918 A | 3/1997 | Eriksson et al. | |
| 5,888,988 A | 3/1999 | Elson | |
| 6,162,241 A | 12/2000 | Coury et al. | |
| 6,165,488 A | 12/2000 | Tardy et al. | |
| 6,166,130 A | 12/2000 | Rhee et al. | |
| 6,458,889 B1 | 10/2002 | Trollsas et al. | |
| 6,458,938 B1 | 10/2002 | Cha et al. | |
| 6,503,527 B1 | 1/2003 | Whitmore et al. | |
| 6,534,591 B2 | 3/2003 | Rhee et al. | |
| 6,602,952 B1 | 8/2003 | Bentley et al. | |
| 6,616,869 B2 * | 9/2003 | Mathiowitz et al. ............ 264/4 |
| 6,699,484 B2 | 3/2004 | Whitmore et al. | |
| 6,730,735 B2 | 5/2004 | Davis et al. | |
| 6,773,723 B1 | 8/2004 | Spiro et al. | |
| 6,806,260 B1 | 10/2004 | Hirofumi et al. | |
| 6,818,018 B1 | 11/2004 | Sawhney | |
| 6,833,408 B2 | 12/2004 | Sehl et al. | |
| 6,884,788 B2 | 4/2005 | Bulpitt et al. | |
| 6,896,904 B2 | 5/2005 | Spiro et al. | |
| 6,899,889 B1 | 5/2005 | Hnojewyj et al. | |
| 6,921,532 B1 | 7/2005 | Austin et al. | |
| 6,936,276 B2 | 8/2005 | Spiro et al. | |
| 6,939,562 B2 | 9/2005 | Spiro et al. | |
| 7,053,068 B2 | 5/2006 | Prinz | |
| 2003/0078234 A1 | 4/2003 | Vournakis et al. | |
| 2004/0052850 A1 | 3/2004 | Schankereli | |
| 2004/0091540 A1 | 5/2004 | Desrosiers et al. | |
| 2004/0156904 A1 | 8/2004 | Saltman et al. | |
| 2004/0166158 A1 | 8/2004 | Davis et al. | |
| 2004/0228794 A1 | 11/2004 | Weller et al. | |
| 2004/0229784 A1 | 11/2004 | Vesely | |
| 2004/0258727 A1 | 12/2004 | Liu et al. | |
| 2004/0258747 A1 | 12/2004 | Ponzoni et al. | |
| 2005/0002893 A1 * | 1/2005 | Goldmann ................ 424/70.27 |
| 2005/0186243 A1 | 8/2005 | Hunter et al. | |
| 2005/0214255 A1 * | 9/2005 | Elson et al. ................. 424/85.7 |
| 2005/0226938 A1 * | 10/2005 | Borbely et al. .............. 424/492 |
| 2005/0238702 A1 | 10/2005 | Ishihara et al. | |

(Continued)

FOREIGN PATENT DOCUMENTS

EP  1462123 A1  9/2004

(Continued)

OTHER PUBLICATIONS

Hitoshi Sashiwa, Naoki Yamamori, Yoshifuni Ichinose, Junzo Sunamtoto and Sci-ichi-Aiba, Chemical Modification of Chitosan, 17a Michael Reaction of Chitosan with Acrylic acid in water, Macromol, Biosci, 3, 231-233, 2003.*

(Continued)

*Primary Examiner*—Michael G Hartley
*Assistant Examiner*—Jagadishwar R Samala
(74) *Attorney, Agent, or Firm*—Goodwin Procter LLP

(57) ABSTRACT

A tissue sealant for use in surgical and medical procedures for sealing the tissues of a living mammal is provided. The tissue sealant comprises a hydrogel which is formed by gelation of a premix disposed on the tissue to be sealed. The premix comprises alkylated chitosan or a gelatin, and a polybasic carboxylic acid or an oxidized polysaccharide, in an aqueous medium. The premix can also include a dehydrating reagent, a carboxyl activating reagent, or both. A specific use of the tissue sealant is in the repair of the dura mater after brain surgery to prevent leakage of cerebrospinal fluid. The tissue sealant may include a therapeutic or protective agent such as an antibiotic or an anti-inflammatory drug.

16 Claims, 3 Drawing Sheets

U.S. PATENT DOCUMENTS

| | | | |
|---|---|---|---|
| 2005/0271729 A1* | 12/2005 | Wang | 424/488 |
| 2006/0014861 A1 | 1/2006 | Geesey et al. | |
| 2006/0029571 A1 | 2/2006 | Karageozian et al. | |
| 2007/0003525 A1 | 1/2007 | Moehlenbruck et al. | |
| 2007/0031467 A1 | 2/2007 | Abrahams et al. | |
| 2007/0031468 A1 | 2/2007 | Abrahams et al. | |
| 2008/0075657 A1 | 3/2008 | Abrahams et al. | |
| 2008/0124395 A1 | 5/2008 | Chen et al. | |
| 2009/0010982 A1 | 1/2009 | Abrahams et al. | |

FOREIGN PATENT DOCUMENTS

| | | |
|---|---|---|
| EP | 1555035 A2 | 7/2005 |
| EP | 1837041 A1 | 9/2007 |
| WO | WO-0197872 | 12/2001 |
| WO | WO-03/035122 | 5/2003 |
| WO | WO-2004006961 A1 | 1/2004 |
| WO | WO-2004/096152 | 11/2004 |
| WO | WO-2005113608 | 12/2005 |
| WO | WO-2006013337 A1 | 2/2006 |
| WO | WO-2007027849 A1 | 3/2007 |
| WO | WO-2007/124198 A3 | 11/2007 |
| WO | WO-2007124198 A2 | 11/2007 |
| WO | WO-2007149130 A1 | 12/2007 |
| WO | WO-2009017753 A2 | 2/2009 |

OTHER PUBLICATIONS

Hitoshi Sashiwa, Naoki Yamamori, Yoshifuni Ichinose, Junzo Sunamtoto and Sci-ichi-Aiba, Chemical Modification of Chitosan, 17a Michael Reaction of Chitosan with Acrylic acid in water, Macromol, Biosci, 3, 231-233, 200.*
H. Jiang, W. Su, M Brant, M.E. De Rosa and T.J. Bunnig, Chitosan-based hydrogels: A new polymer-based system with excellent laser-damage threshold properties, Journal of Polymer Science: Part B: Polymer Physics vol. 37, 769-778 (1999).*
"U.S. Appl. No. 11/379,182, Non-Final Office Action mailed Dec. 12, 2008", 12 pgs.
"U.S. Appl. No. 11/425,280 Non-Final Office Action mailed Jan. 23, 2009", 31 pgs.
"U.S. Appl. No. 11/447,794, Non-Final Office Action mailed Jan. 8, 2009", 14 pgs.
"U.S. Appl. No. 11/447,794, Non-Final Office Action mailed Jul. 22, 2008", 12 pgs.
"U.S. Appl. No. 11/447,794, Response filed Apr. 9, 2008 to Restriction Requirement mailed Mar. 19, 2008", 7 pgs.
"U.S. Appl. No. 11/447,794, Response filed Sep. 22, 2008 to Non-Final Office Action mailed Jul. 22, 2008", 12 pgs.
"U.S. Appl. No. 11/447,794, Restriction Requirement mailed Mar. 19, 2008", 8 pgs.
"International Application Serial No. PCT/US2008/007234, International Search Report mailed Apr. 2, 2009".
"International Application Serial No. PCT/US2008/007234, Written Opinion mailed Apr. 2, 2009".
"International Application Serial No. PCT/US2008/009198, International Search Report mailed Apr. 9, 2009".
"International Application Serial No. PCT/US2008/009198, Written Opinion mailed Apr. 9, 2009".
Abrahams, J. M, et al., "Delivery of human vascular endothelial growth factor with platinum coils enhances wall thickening and coil impregnation in a rat aneurysm model", AJNR Am J Neuroradiol, (2001) 1410-1417.
Athanasiadis, Theo, et al., "Effects of a Novel Chitosan Gel on Mucosal Wound Healing Following Endoscopic Sinus Surgery in a Sheep Model of Chronic Rhinosinusitis", The Laryngoscope 118, (Jun. 2008), 1088-1094.
Borzacchiello, A., et al., " Chitosan-based hydrogels: Synthesis and Characterization", Journal of Materials Science, 12, 861-864.
Borzacchiello, A., et al., "Chitosan-based hydrogels: Synthesis and characterization", Journal of Materials Science: Materials in Medicine, 12(10-12), (Dec. 2001), 861-864.

Chenite, A., et al., "Novel injectable neutral solutions of chitosan form biodegradable gels in situ", (2000), 2155-2161.
Crescenzi, V., et al., "New hydrogels based on carbohydrates and carbohydrate-synthetic polymer networks", Polymer gels and networks. 5 (1997), 225-239.
Di Martino, A., et al., "Chitosan: A Versatile biopolymer for orthopaedic tissue-engineering", Biomaterials, Elsevier Science Publishers B.V., Barking, vol. 26, No. 30, (Oct. 1, 2005), 5986.
Freier, T., et al., "Controlling, sell adhesion and degradation of chitosan films by N-acetylation", Biomaterials 26, (2005), 5872-5878.
Kang, Q. K, et al., "Arterial embolization using Poly-N-Acetyl glucosamine gel in a rat kidney model", The anatomical record part A 284A, (2005), 454-459.
Mwale, F., et al., "Biological evaluation of chitosan salts cross-linked to genpin as a cell scaffold for disk tissue engineering", Tissue engineering, vol.11, No. 1-2, (Jan.-Feb. 2005), 130-140 pgs.
Ribourtout, E., et al., "Gene Therapy and endovascular treatment of intracranial aneurysms", Stroke: 35, (2004), 786-793.
Riha, G. M. et al., "Application of stem cells for vascular tissue engineering", Tissue engineering11(9/10), 2005, 1535-1552.
Sashiwa H. et al., " Michael Reaction of Chitosan with Acrylic Acid in Water", Macromol Biosci3, (2003), 231-233 pgs.
Schiele, U., et al., "Haemostyptic Preparations on the Basis of Collagen alone and as fixed Combination with Fibrin Glue", Clinical Materials, Elsevier, vol. 9, No. 3-4, (Jan. 1, 1992), 169-177 pgs.
Heras et al. (2001) "N-methylene phosphonic chitosan: a novel soluble derivative," Carbohydrate Polymers 44:1-8.
Holme, et al. (1997) "Chitosan N-sulfate. A Water-soluble polyelectrolyte," Carbohydrate Research 302:7-12.
Jayakumar et al. (2007) "Sulfated chitin and chitosan as novel biomaterials," International Journal of Biological Macromolecules 40:175-181.
Jia et al. (2001) "Synthesis and antibacterial activities of quaternary ammonium salt of chitosan," Carbohydrate Research 333:1-6.
Kato et al. (2004) "N-succinyl-chitosan as a drug carrier: water-insoluble and water-soluble conjugates," Biomaterials 25:907-915.
Sugimoto et al. (1998) "Preparation and characterization of water-soluble chitin and chitosan derivatives," Carbohydrate Polymers 36:49-59.
Xie et al. (2002) "Preparation and antibacterial activity of a water-soluble chitosan derivative," Carbohydrate Polymers 50:35-40.
Xu et al. (2003) "Preparation and modification of N-(2-hydroxyl) propyl-3-trimethyl ammonium chitosan chloride nanoparticle as a protein carrier," Biomaterials 24:5015-5022.
Yang et al. (2005) "Adsorption of Metal Cations by Water-Soluble N-Alkylated Disaccharide Chitosan Derivatives," Journal of Applied Polymer Science 98:564-570.
Yuan et al. (2008) "Self healing in polymers and polymer composites. Concepts, realization and outlook: A review," xPRESS Polymer Letters 2(4):238-250.
Material Safety Data Sheet: Acetic Acid 10% v/v Aqueous Solution.
Material Safety Data Sheet: Methyl Alcohol, Reagent ACS, 99.8% (GC).
Material Safety Data Sheet: Acetic Anhydride.
Material Safety Data Sheet: N, N'-Methylenebisacrylamide.
"DuraSeal Sealant System", http://www.confluentsurgical.com/prod_ds_ous.html, (2006),2 pgs.
"Polyethylene Glycol and Derivatives for Advanced PEGylation", Nektar Advanced PEGylation Catalog 2005-2006. (2005),34 pgs.
"Polyethylene Glycol and Derivatives for Advanced PEGylation", Catalog 2005-2006 Nektar Advanced PEGylation, www.nektar.com/pdf/nektar_catalog.pdt,(2005),34 pgs.
"U.S. Appl. No. 11/425,280, Preliminary Amendment mailed Feb. 19, 2007", 13 pgs.
"U.S. Appl. No. 11/379,182, Non-Final Office Action mailed Dec. 21, 2007", OARN,10 pgs.
"U.S. Appl. No. 11/379,182, Restriction Requirement mailed Oct. 2, 2007", 7 pgs.
"International Application Serial No. PCT/US 07/01606, International Search Report mailed Oct. 23, 2007", 4 pgs.
"International Application Serial No. PCT/US 07/01606, Written Opinon mailed Oct. 23, 2007", 7 pgs.

Profeta, et al., "Endoscope-Assisted microneurosurgery for anterior circulation aneurysms using the angle-type rigid endoscope over a 3-year period", *Child Nerv. Syst.*,20(11-12), Epub Jun. 23, 2004(Nov. 2004),811-815.

"U.S. Appl. No. 11/379,182, Response filed Aug. 22, 2008 to Restriction Requirement mailed Aug. 6, 2008", 18 pgs.

"U.S. Appl. No. 11/379,182, Response filed Nov. 1, 2007 to Restriction Requirement mailed Oct. 2, 2007", 12 pgs.

"U.S. Appl. No. 11/379,182, Restriction Requirement mailed Aug. 6, 2008", 8 pgs.

"U.S. Appl. No. 11/425,280, Response filed Jul. 16, 2008 to Restriction Requirement mailed Jun. 24, 2008", 7 pgs.

"U.S. Appl. No. 11/425,280, Response filed Nov. 6, 2008 to Restriction Requirement mailed Oct. 30, 2008", 7 pgs.

"U.S. Appl. No. 11/425,280, Restriction Requirement mailed Jun. 24, 2008", 10 pgs.

"U.S. Appl. No. 11/425,280, Restriction Requirement mailed Oct. 10, 2008", 6 pgs.

"International Application Serial No. PCT/US2007/062393, Preliminary Report on Patentability mailed Oct. 30, 2008", 8 pgs.

"U.S. Appl. No. 11/379,182 Response to Non-Final Office Action filed Apr. 9, 2008", 19 pgs.

"International Application No. PCT/US2007/001606 Demand and Article 34 Amendment filed Apr. 10, 2008", 24 pgs.

"International Application Serial No. PCT/US2007/062393, Search Report and Written Opinion mailed on Aug. 19, 2008".

"Polyethylene Glycol and Derivatives for Advanced PEGylation", *Catalog 2005-2006 Nektar Advanced PEGylation*www.nektar.com/pdf/nektar_catalog.pdt, (2005), 34 pgs.

Shu, X. Z, et al., "Disulfide-Crosslinked hyaluronan-gelatin hydrogel films: a covalent cell growth", *Biomaterials*;vol.(24), (2003), 3825-3834.

Aiba, Sei-Ichi , et al., "Application of chitin and chitosan to functional materials; Organo- and water-soluble chitosan derivative and N-acetyl-D-glucosamine", *National Institute of Advanced Industrial Science and Technology (AIST)*, Ikeda, Osaka, Japan,(2004), 2 pgs.

Bartkowiak, A. , et al., "Alginate-Oligochitosan Microcapsules: a Mechanistic Study Relating Membrane and Caps operties to Reaction Conditions", Chemistry of Materials, 11(91, (Sep. 1999),2486-2492.

Campbell, Patrick K., et al., "Evaluation of Absorbable Surgical Sealants: In vitro Testing", www.duralsealant.com/duralsealant/literature.htm, (2005),4 pgs.

Cargioli, Theresa G., http://www.sinc.sunysb.edu/Stu/tcargioi/Research.htm, (2006),3 pgs.

Grotenhuis, J A., "A Novel Absorbable Hydrogel for Dural Repair: Results of a Pilot Clinical Study", *Confluent Surgical*, http://www.confluentsurgical.com/pdf/ds/DuraSeal_Pilot_Study_WP4-7-05.pdf, (2005),4 pgs.

Hennink, W E., et al., "Novel crosslinking methods to design hydrogels", *Adv Drug Deliv Rev.*, 54(1), (Jan. 17, 2002), 13-36.

Hollander, Anthony P., et al., "Chapters 3 & 4", *Biopolymer methods in tissue engineering / edited by Anthony P. Hollander and Paul V. Hatton*, Totowa, N.J. : Humana Press,(2004),24-48.

Leach, Jennie B., et al., "Photocrosslinked Hyaluronic Acid Hydrogels: Natural, Biodegradable Tissue Engineering Scaffolds", *Biotechnology and Bioengineering*, vol. 82, No. 5,(Jun. 5, 2003), 578-589.

Sanzgiri, Y. D., et al., "Synthesis, characterization, and in vitro stability of chitosan-methotrexate conjugates", *Pharm Res.*, 7(4). (Apr. 1990), 418-21.

Sashiwa, H. , et al., "Michael Reaction of Chitosan with Various Acryl Reagents in Water", *Biomacromolecules*, 4(5), (Sep.-Oct. 2003), 1250-1254.

Sezer, A. D., et al., "Release characteristics of chitosan treated alginate beads: II. Sustained release of a low molecular drug from chitosan treated alginate beads", *J Microencapsul.*, 16(6), (Nov.-Dec. 1999),687-96.

Spotnitz, W. D., et al., "Fibrin Glue from Stored Human Plasma: An Inexpensive and Efficient Method for Local Blook Bank Preparation", *The American Surgeon*, 53, (1987),460-62.

* cited by examiner

BIOPOLYMER SYSTEM FOR TISSUE SEALING

CLAIM OF PRIORITY FROM A PRIOR-FILED APPLICATION

This application is a continuation-in-part of U.S. patent application Ser. No. 11/379,182, filed Apr. 18, 2006, which is incorporated herein by reference, and claims the priority thereof.

FIELD OF THE INVENTION

The invention relates to tissue sealants for medical or veterinary use, methods of preparing the sealants, and methods of using them in medical procedures.

BACKGROUND OF THE INVENTION

Tissue sealants are increasingly important adjuncts in surgical procedures, being used in fields such as vascular surgery, cardiac surgery, spine surgery and brain surgery as well as in general surgery. Uses for tissue sealants include, among others, augmenting or replacing sutures to join tissues or place them in proximity, closing perforations in biological membranes to prevent leakage of fluids, incorporating medicinal substances at the location of emplacement for localized release, and filling areas of tissue removal. One commonly used tissue sealant is fibrin glue, a material analogous to clotted blood, which is obtained from reaction of fibrinogen and thrombin isolated from blood plasma. For example, see "Fibrin Glue from Stored Human Plasma: An Inexpensive and Efficient Method for Local Blood Bank Preparation," William D. Spotnitz, M. D., Paul D. Mintz, M. D., Nancy Avery, M. T., Thomas C. Bithell, M. D., Sanjiv Kaul, M. D., Stanton P. Nolan, M. D. (1987), *The American Surgeon*, 53, 460-62. However, concern about possible viral or prion contamination of human blood-derived protein products, and dissatisfaction with the relatively long times often required for fibrin gelation or "setting" to occur, have resulted in a search for tissue sealants with more advantageous properties.

There have been systems developed that use fibrin glues as part of a more complex assembly with more favorable properties. U.S. Pat. No. 6,699,484 discusses the use of fibrinogen in mixtures with polysaccharides such as hyaluronan and chitosan to form surgical adhesives, wherein the fibrinogen and thrombin components are distributed in dry form on a support comprising the polysaccharide, which is activated by water when emplaced on a wound to form a sealant.

In an attempt to avoid the use of human blood products, other mammalian sources of proteins have been studied. A tissue sealant has been prepared using bovine serum albumin that is crosslinked with glutaraldehyde. An example is Bio-Glue Surgical Adhesive® produced by CryoLife, Inc. of Kennesaw, Ga. However, bovine tissues are also a source of concern in terms of the possible presence of pathogenic entities such as viruses or prions. The types of processing required to destroy viruses or prions also tend to denature the desired proteins and make them intractable as sealants.

A tissue sealant that does not use proteins isolated from mammalian blood, such as Duraseal® produced by Confluent Surgical Inc. of Waltham, Mass., comprises tri-lysine-amine and an activated polyethyleneglycol. A similar product, termed CoSeal® and produced by Baxter of Deerfield, Ill., is likewise composed of synthetic functionalized polyethyleneglycol derivatives, also avoiding the use of blood-derived materials. However, both of these synthetic hydrogels are dimensionally unstable in the presence of water, undergoing considerable swelling. For example, see "Evaluation of Absorbable Surgical Sealants: In vitro Testing," Patrick K. Campbell, PhD, Steven L. Bennett, PhD, Art Driscoll, and Amar S. Sawhney, PhD, at www.duralsealant.com/duralsealant/literature.htm (as of Aug. 24, 2006). This tendency to swell can be highly disadvantageous in certain applications, such as neurosurgery, where the resulting pressure on nerve or brain tissue can produce serious side-effects.

Chitin, a biopolymer that is abundant in the shells of arthropods, is a β-1,4 polymer of 2-acetamido-2-deoxyglucose. During its isolation, it is freed from proteinaceous and mineral components of the shell. Purified chitin can be further processed by chemical treatment resulting in deacetylation to yield chitosan, (poly-(2-amino-2-deoxyglucose)), which is a basic (alkaline) substance due to its free amino groups. From the perspective of medical uses, chitosan offers several desirable properties. The material is known to be non-toxic and biocompatible, and since chitin is not derived from vertebrates and is processed under rather harsh conditions such as exposure to alkalai during its transformation into chitosan, the possibility of contamination with viruses or prions that are pathogenic to mammals is very low. The utility of biocompatible chitosan derivatives in medical applications has received attention. For example, U.S. Pat. No. 5,093,319 discusses the use of films prepared from carboxymethylated chitosan for use in surgery to prevent post-operative adhesion of injured soft tissues upon healing. The chitosan derivatives are described to be formed into a biodegradable "sheet" that during surgery is emplaced between soft tissues for which adherence during healing is not desired. In another type of use, U.S. Pat. No. 4,532,134 discusses the use of chitosan in promoting blood coagulation in wounds.

Hydrogels are gels in which water is the dispersion medium. A common example of a hydrogel is a gel formed from the protein gelatin in water. Other hydrogels are formed by polysaccharides such as agar dispersed in water. Hydrogels in the form of sheets are used as wound dressings, where they are favored for their ability to help maintain a moist environment to facilitate healing of the wound without drying and cracking of tissues. For example, see www.medicaledu.com/hydrogellsheet.htm. Chemical derivatives of chitosan have also been used to form hydrogels for use as surgical sealants and in drug delivery devices. U.S. Pat. No. 6,602,952, assigned to Shearwater Corp., describes the preparation of poly(alkyleneoxide)chitosan derivatives and their use in the formation of hydrogels. The addition of these hydrophilic but non-ionic groups to the chitosan molecule alters its physical properties. Poly(alkyleneoxides) such as poly(ethyleneoxide), also known (somewhat inaccurately) as poly-ethyleneglycols or PEGs, are formed by the polymerization of alkylene oxides (epoxides) such as ethylene oxide. They may be obtained in a wide variety of molecular weights, with various structural features such as activated end groups, hydrolysable linkages, and others. For example, see the Nektar PEG catalog that lists a wide variety of the Shearwater functionalized PEGs, at www.nektar.com/pdf/nektar_catalog.pdf (as of Aug. 24, 2006).

Other methods have been described for the preparation of hydrogels from chitosan. The published PCT application WO2005/113608 and the published U.S. patent application no. 2005/0271729, both by the same inventor, discuss the crosslinking of chitosan and hyaluronan, also known as hyaluronic acid. Hyaluronan is an acidic linear polysaccharide formed of β-1,3 linked dimeric units, the dimeric units consisting of an 2-acetamido-2-deoxyglucose and D-gluconic acid linked in a β-1,4 configuration. These published applications discuss crosslinking the two types of polysaccharides using a carbodiimide reagent.

Hydrogels comprising chitosan derivatives and polybasic carboxylic acids or oxidized polysaccharides, for use in vascular occlusion, are also disclosed in copending U.S. patent application Ser. No. 11/425,280, filed Jun. 20, 2006 by the same inventors as in the present application.

There is an ongoing need for a hydrogel tissue sealant that is not blood or animal protein derived, that consists of biocompatible materials, is dimensionally stable after emplacement in the patent's body, has good sealant and tissue adhesive properties, is of sufficient strength and elasticity to effectively seal biological tissues, that can be readily prepared and used during surgery, and that forms the tissue seal on a timescale compatible with surgery on living patients.

SUMMARY OF THE INVENTION

The present invention provides a tissue sealant for medical or veterinary use in repair of physical damage to living mammalian tissues such as cuts, tears, holes, bone breaks and other unintentional injury.

The invention further provides a tissue sealant for medical or veterinary use in repair of physical damage resulting from surgical procedures, such as in closing a suture line, reinforcing a suture line, tissue approximation using the sealant instead of a suture, filling a disused dead space or void, or sealing a vascular defect.

The invention further provides a tissue sealant useful in medical procedures such as in preventing post-surgical adhesions, as a mechanism of drug delivery, or in coating implanted medical devices.

The invention further provides a tissue sealant that is well-suited for the repair and sealing of membranous biological tissues, in particular the dura mater and other membranes surrounding neural tissue.

The invention further provides a tissue sealant that due to its exceptional dimensional stability may be used in situations where swelling and the resulting pressure are undesirable and produce unwanted side effects.

The invention further provides a tissue sealant that offers a very low risk of contamination by pathogens such as viruses and prions.

The invention further provides a tissue sealant that is not prepared from human blood products, which is desirable because human blood products carry a risk of contamination with pathogens and are also objectionable to certain patients on religious and moral grounds.

The invention further provides a premix, a flowable, substantially liquid sol, that on standing forms a hydrogel that seals biological tissues, preferably adhering to the tissues.

A composition of the invention can comprise a chitosan derivative that has been modified by the introduction of covalently bound moieties onto the polymer chain. The chitosan derivative, and a polybasic carboxylic acid or an oxidized polysaccharide, upon dissolution in an aqueous medium can initially form a flowable, substantially liquid sol, a premix, that over a period of time, typically in the order of minutes, gels to form a hydrogel of the invention. The hydrogel, which is biocompatible and can be biodegradable, when formed serves to seal tissues that have been cut or torn, for example from a surgical procedure or from an injury. The hydrogel can also adhesively seal tissues.

The invention further provides an embodiment of a premix comprising a poly(oxyalkylene)chitosan and a hyaluronan. In another embodiment according to the present invention, the premix comprises an acrylated chitosan and a dibasic carboxylic acid.

The invention further provides a premix for a hydrogel tissue sealant comprising an alkylated chitosan, a polybasic carboxylic acid, a carboxylic acid activating reagent, a dehydrating reagent, and an aqueous medium. The carboxyl activating reagent can be an N-hydroxy compound that can form an ester with the carboxyl group, preferably N-hydroxysuccinimide (NHS) or N-hydroxybenztriazole. The dehydrating reagent can be a carbodiimide that removes the elements of water from reactants by thermodynamically driving the reaction, through formation of a urea compound. In one embodiment, the specific carbodiimide is 1-ethyl-3-(N,N-dimethylpropyl)carbodiimide (EDCI).

The invention also provides an embodiment of a flowable aqueous sol comprising a gelatin and an oxidized polysaccharide. A specific example is a composition comprising gelatin and oxidized hyaluronan.

The invention further provides methods for preparing the tissue sealants as are described herein for medical or veterinary use. The tissue sealants comprise a hydrogel that preferably adheres to the biological tissue of a living mammal. A specific method of preparation of a tissue sealant comprising a hydrogel according to the present invention is through combination of an alkylated chitosan, and a polybasic carboxylic acid or an oxidized polysaccharide in an aqueous medium. Optionally, a dehydrating reagent, a carboxyl-activating reagent, or both, may be included.

The invention further provides methods for using a hydrogel according to the present invention in tissue repair and other medical procedures. A specific embodiment of a hydrogel according to the present invention is used to reinforce a suture line, or to seal cut, torn, or perforated tissues. It is also used to prevent leakage of biological fluids, such as cerebrospinal fluid, through repair of biological membranes that when intact contain the fluids. It is used to bring tissues into approximation and hold them in place after a surgical procedure has been carried out.

In another specific embodiment of a use of a hydrogel according to the present invention, the hydrogel may further comprise a protective or therapeutic material or substance. The substance may be an antibiotic, an anticancer agent, a peptide, a protein, a nucleic acid or a nucleic acid analog, a radioactive material, or another protective or therapeutic substance where it is advantageous to provide the substance at the location within the body where the hydrogel is emplaced.

For example, the protein may be a growth factor, such as a vascular growth factor or a factor that induces a particular kind of tissue growth, such as bone morphogenic factor. In another specific embodiment, the protein may be an inhibitory factor, such as a receptor antagonist such as for a growth factor, when supply of an inhibitory factor is desirable, for example after removal of a tumor or cancerous tissue.

In yet another specific embodiment, the nucleic acid may be an antisense nucleic acid, or a small interfering nucleic acid analog, wherein it is advantageous to securely emplace the material at a particular site within a living mammal undergoing treatment for a condition responsive to such therapy.

In another specific embodiment, the therapeutic agent may be an antibiotic to inhibit bacterial infection after repair of a wound or after damage to tissues caused by surgery. Or, a protective agent may be an anti-inflammatory substance wherein it is advantageous to supply the substance directly at the site of damage that is repaired with the tissue sealant, such as to reduce swelling and resulting pressure on surrounding tissues.

In another specific embodiment, the hydrogel comprises a dye, such as a visible dye or a radio-opaque dye, to enable visualization of the position of localization of the hydrogel in the body.

In another specific embodiment, the hydrogel comprises a microsphere or a nanosphere, preferably a large number of microspheres or nanospheres dispersed in the hydrogel. Preferably the microsphere or nanosphere contains a therapeutic agent or a protective agent.

Thus, the hydrogels of the present invention, and their uses as tissue sealants, as media further containing therapeutic or protective agents, and as tissue sealants further containing therapeutic or protective agents, offer outstanding advantages of ease of use, biocompatibility and biodegradability, suitability for use in conjunction with other surgical procedures, strength, adhesivity, and versatility.

DETAILED DESCRIPTION OF THE INVENTION

Definitions

Figure 1:
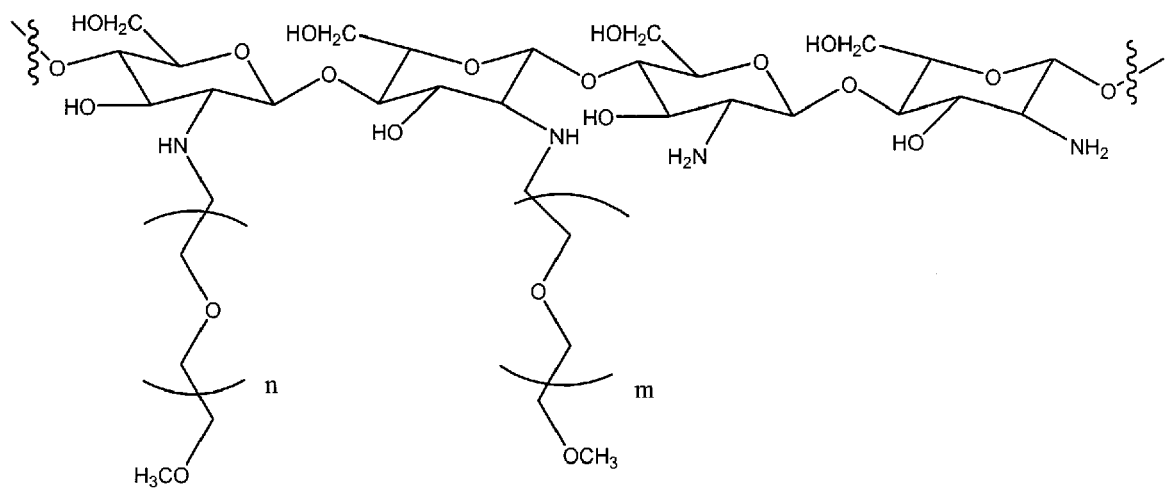
FIG. 1 shows the chemical structure of a segment of a PEG-chitosan molecule wherein the degree of substitution with the PEG group is 0.5.

As used herein, "tissue" refers to the material forming the solid or semi-solid structures that make up any of the organs or components of a living organism. Thus, liquids such as blood are not "tissue" according to the definition used herein, but the term "tissue" encompasses membranes, skin, muscles, bones, cartilage, nerves and nerve sheaths, meninges, connective tissue, blood vessels, the sclera or iris of the eye, the solid materials constituting internal organs such as liver, stomach, pancreas, intestine, kidney, thymus, uterus, testes, bladder, lung, heart and any other internal structures that are solid or semi-solid in texture.

As used herein, the term "to seal" or "sealing" refers to the act wherein two physically noncontiguous tissues or portions thereof are joined together, or where a hole, tear, cut, perforation or other discontinuity is repaired so as to close the hole, tear, cut or perforation. Sealing implies at least some degree of adhesion of the material used to the tissue to which it is applied, such that the sealed tissue is secured against at least a moderate displacing force. The discontinuity in the tissue that is being sealed may be an incision made as part of a surgical procedure, or it may be a wound. A "sealant" is a material which is used to seal tissue. As mentioned, a sealant adheres, at least to some degree, to the tissue which is being sealed, such that the sealant material is unlikely in the short term to detach from the repaired or sealed tissue under the influence of at least a moderate force, such as may be experienced when a patient to whom the sealant has been applied moves in a normal fashion. The sealant may be biodegradable and eventually dissolve or be absorbed into the patient's body without departing from the principles of the invention.

The degree of force that is needed to disrupt a seal formed according to the invention may vary. If the tissue is "sealed", as the term is used herein, the degree of adhesivity may be relatively low, such that the sealant serves to fill a void in the tissue or to keep the tissue portions in conjunction when they are not subject to a high degree of strain. If a tissue is "adhesively sealed," as the term is used herein, a higher degree of strain is necessary to disrupt the bond between the tissue portions, such that rupture of the seal only takes place when a relatively high degree of force is applied. Thus, a tissue may be sealed such that the joined tissue portions are held in proximity by a sealant but application of a relatively high degree of strain would tend to separate the portions and rupture the seal, or the tissue may be adhesively sealed such that a relatively high degree of strain is needed to rupture the seal.

"Adhere" or "adherence" refers to the creation of a physical bond between the material and tissue such that a moderate motion or force does not cause separation of the material from the tissue on which it is disposed. Thus, a tissue sealant serves to glue together living tissue, at least temporarily, such as for the amount of time it takes healing to occur. However, sealing may take place for a more prolonged period without departing from the principles of the invention. The physical bond that is created between the material and the tissue that is being sealed may have one or several bases including electrostatic bonding and covalent bonding, but any mechanism by which the adherence takes place falls within the definition herein.

The terms "adhesive" and "adhesivity" similarly refer to the existence of a physical bond between two materials such as a tissue sealant and the tissue to which the sealant is applied. An adhesive is a material which adheres to tissue or other material and which may be used to constrain the separation of two tissue masses. Adhesivity is the property or degree to which a material adheres to a tissue or other material. As used herein, adhesive tissue sealants are those sealants of the invention that are adapted to hold the tissue portions being sealed together against a relatively high degree of rupturing strain.

As used herein, a "hydrogel" refers to a material of solid or semi-solid texture that comprises water. Hydrogels are formed by a three-dimensional network of molecular structures within which water, among other substances, may be held. The three-dimensional molecular network may be held together by covalent chemical bonds, or by ionic bonds, or by any combination thereof. A common example of a hydrogel is gelatin, a protein, that "sets up" or forms a gel from a sol upon heating and subsequent cooling. Not all substances that form hydrogels are proteins; polysaccharides such as starches may also form hydrogels. Still other hydrogels may be formed through the mixture of two or more materials that undergo chemical reactions with each other to create the three-dimensional molecular network that provides the hydrogel with a degree of dimensional stability. Such mixtures of materials that interact or react with each other to form a hydrogel are referred to herein as a "premix." Thus, a "premix" as used herein refers to a mixture of materials that after mixing will gel, or "set up," to form the hydrogel. A premix may be of a liquid or semi-liquid texture such that it can be pumped or transferred by the methods usually used for liquids, such as flow through tubes.

The act of "gelation" refers to the formation of a gel from a sol. In some cases, the sol may consist of a single material dispersed in a solvent, typically water, as in the case of gelatin. In other cases, the sol may consist of more than a single material dispersed in a solvent wherein the several materials will eventually react with each other to form a gel, and when the solvent in which they are dispersed comprises water, the gel is a hydrogel. The hydrogels claimed herein are of the type that are formed by the mixture of more than a single component.

A "saccharide" as used herein refers to a carbohydrate. The term "carbohydrate" includes the class of compounds commonly known as sugars, in addition to compounds that are chemically related to sugars. The term thus includes simple "monosaccharide" sugars, "disaccharide" sugars as well as polymeric "polysaccharides.". The term encompasses a group of compounds including sugars, starches, gums, cellulose and hemicelluloses. The term further encompasses sugar derivatives such as amino-sugars, for example, 2-amino-2-deoxyglucose, as well as their oligomers and polymers; sulfated sugars; and sugars with hydroxyl, amino, carboxyl and other groups.

A carbohydrate as defined herein comprises sugars or sugar derivatives with beta (β) or alpha (α) anomeric stereochemistry; moreover, the sugars can have (R) or (S) relative configurations, can exist as the (+) or (−) isomer, and can exist in the D or L configuration. The terms "anomer" and "anomeric" refer to the stereochemical configuration at the acetal, hemiacetal, or ketal carbon atom, as is well known in the art.

As used herein, "chitosan" refers to a polysaccharide polymer, either obtained from a natural source such as chitin, or synthetically prepared. Chemically, chitosan is predominantly a polymer of β-1,4-linked 2-amino-2-deoxyglucose monomers. When prepared from a natural source, the usual natural source is chitin, a major constituent of the shells of crabs, shrimp and other arthropods. Chitin is chemically a polymer comprising β-1,4-linked 2-acetamino-2-deoxyglucose monomers. After isolation of chitin from its natural source, it is treated in a manner as to cause hydrolysis of the acetamido group without cleavage of the sugar-sugar bonds, typically through alkaline hydrolysis. Chitosan is not a single molecular entity, but comprises polymeric chains of various lengths.

As used herein, an "alkylated chitosan" is a material formed of chitosan molecules to which carbon-containing molecules have been bonded. The term "alkylated chitosan" thus comprises a large number of possible chemical structures, but they all share the unifying feature that chemical bonds have been formed between the components of the chitosan molecules and at least one carbon atom in each of the molecules that are bonded to the chitosan. For example, methylation of chitosan, in which bonds are formed between methyl radicals or groups and atoms within the chitosan molecule, such as nitrogen, oxygen or carbon atoms, provides an alkylated chitosan within the definition used herein. Other carbon-containing groups may likewise be chemically bonded to chitosan molecules to produce an alkylated chitosan. Specific examples include poly(oxyalkylene)chitosan, wherein poly(oxyethylene), or polyethyleneglycol, chains are covalently bonded to the chitosan backbone, as well as acrylated chitosans, formed by alkylation of chitosan with acrylates.

When referring to the "molecular weight" of a polymeric species such as an alkylated chitosan, a weight-average molecular weight is being referred to herein, as is well known in the art.

A "degree of substitution" of a polymeric species refers to the ratio of the average number of substituent groups, for example an alkyl substituent, per monomeric unit of the polymer as defined.

A "degree of polymerization" of a polymeric species refers to the number of monomeric units in a given polymer molecule, or the average of such numbers for a set of polymer molecules.

A "poly(oxyalkylene)chitosan" is a variety of alkylated chitosan as defined herein. A "poly(oxyalkylene)" group is a polymeric chain of atoms wherein two carbon atoms, an ethylene group, are bonded at either end to oxygen atoms. The carbon atoms of the ethylene group may themselves bear additional radicals. For example, if each ethylene group bears a single methyl group, the resulting poly(oxyalkylene) group is a poly(oxypropylene) group. If the ethylene groups are unsubstituted, the poly(oxyalkylene) group is a poly(oxyethylene) group. A poly(oxyethylene) group may be of a wide range of lengths, or degrees of polymerization, but is of the general molecular formula of the structure [—$CH_2$—$CH_2$—O—$CH_2$—$CH_2$—O—]$_n$, where n may range from about 3 upwards to 10,000 or more. Commonly referred to as "polyethyleneglycol" or "PEG" derivatives, these polymeric chains are of a hydrophilic, or water-soluble, nature. Thus, a poly(oxyalkylene)chitosan is a chitosan derivative to which poly(oxyalkylene) groups are covalently attached. A terminal carbon atom of the poly(oxyalkylene) group forms a covalent bond with an atom of the chitosan chain, likely a nitrogen atom, although bonds to oxygen or even carbon atoms of the chitosan chain may exist. Poly(oxyethylene)chitosan is often referred to as "polyethyleneglycol-grafted chitosan" or "PEG-chitosan" or "PEG-g-chitosan" or "PEG-grafted-chitosan."

The end of the poly(oxyethylene) chain that is not bonded to the chitosan backbone may be a free hydroxyl group, or may comprise a capping group such as methyl. Thus, "polyethylene glycol" or "poly(oxyethylene)" or "poly(oxyalkylene)" as used herein includes polymers of this class wherein one, but not both, of the terminal hydroxyl groups is capped, such as with a methyl group. In a specific method of preparation of the poly(oxyethylene)chitosan, use of a polyethyleneglycol capped at one end, such as MPEG (methyl polyethyleneglycol) may be advantageous in that if the PEG is first oxidized to provide a terminal aldehyde group, which is then used to alkylate the chitosan via a reductive amination method, blocking of one end of the PEG assures that no difunctional PEG that may crosslink two independent chitosan chains is present in the alkylation reaction. It is preferred to avoid crosslinking in preparation of the poly(oxyethylene) chitosans of the present invention.

FIG. 1 provides an example of the chemical structure of a segment of a poly(oxyethylene)chitosan polymer.

Figure 4:
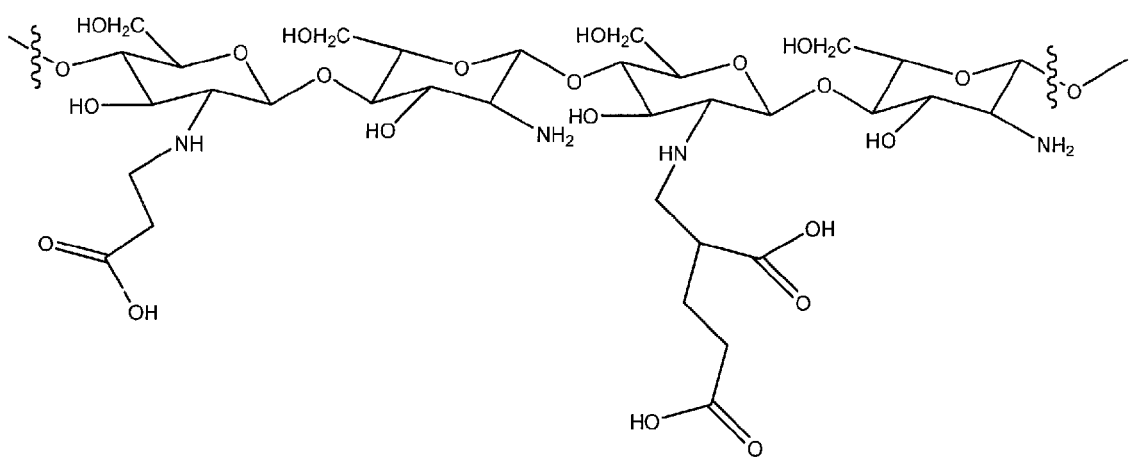
FIG. 4 shows a segment of an acrylated chitosan polymer.

An alkylated chitosan is also a chitosan to which other carbon-containing molecules are linked. An "acrylated chitosan" as the term is used herein is an alkylated chitosan wherein acrylates have been allowed to react with, and form chemical bonds to, the chitosan molecule. An acrylate is a molecule containing an α,β-unsaturated carbonyl group; thus, acrylic acid is prop-2-enoic acid. An acrylated chitosan is a chitosan wherein a reaction with acrylates has taken place. The acrylate may bond to the chitosan through a Michael addition of the chitosan nitrogen atoms with the acrylate. FIG. 4 provides an example of the chemical structure of a segment of an acrylated chitosan polymer.

Figure 2:
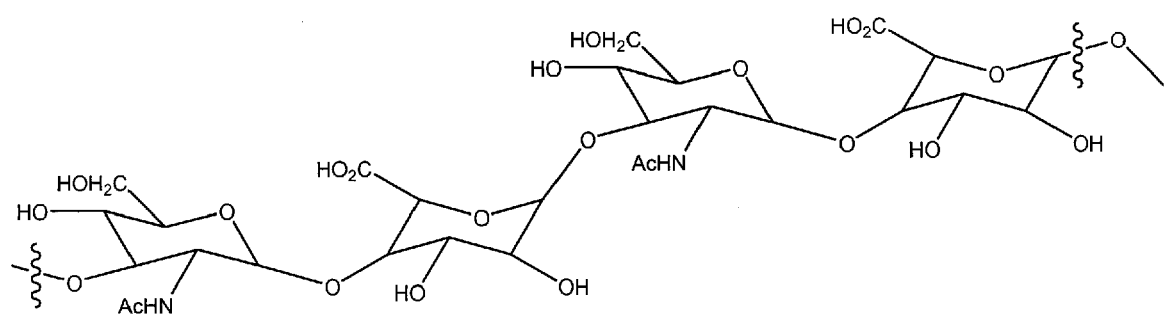
FIG. 2 shows the chemical structure of a segment of a hyaluronan molecule.
Figure 3:
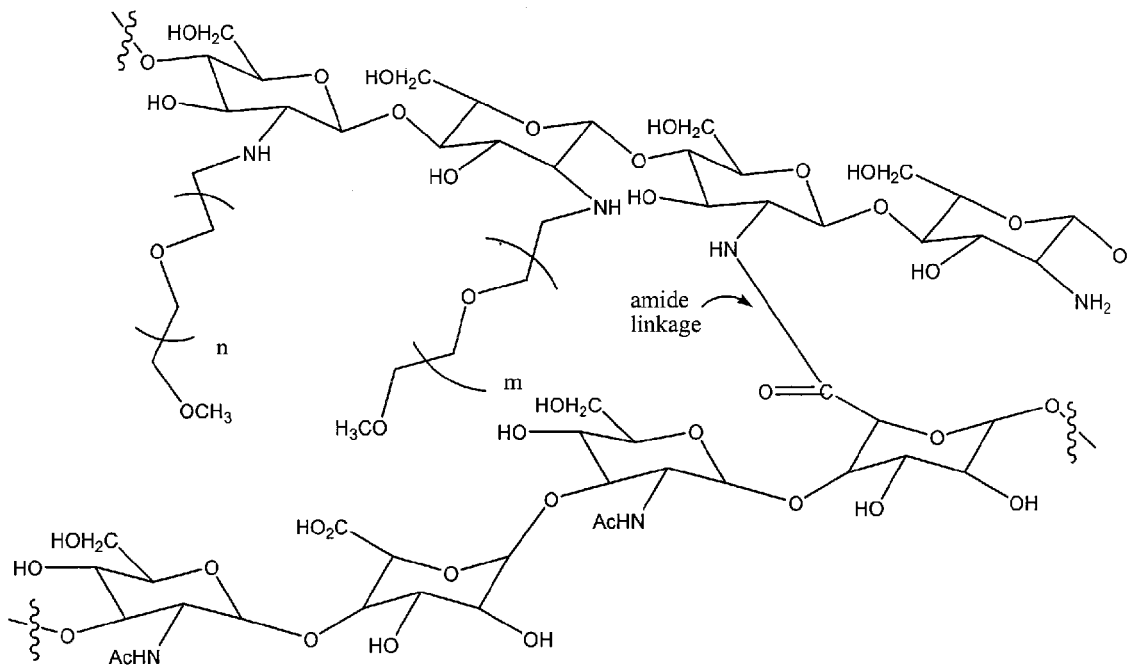
FIG. 3 shows the chemical structure of a segment of the PEG-chitosan of FIG. 1 and a segment of the hyaluronan of FIG. 2 crosslinked by amide linkages between a hyaluronan carboxylate moiety and a PEG-chitosan amino moiety.

As used herein, a "polybasic carboxylic acid" means a carboxylic acid with more than one ionizable carboxylate residue per molecule. The carboxylic acid may be in an ionized or salt form within the meaning of the term herein. A dibasic carboxylic acid is a polybasic carboxylic acid within the meaning herein. Thus, adipic acid is a polybasic carboxylic acid, having two ionizable carboxylate residues per molecule. Disodium adipate is a polybasic carboxylic acid within the meaning of the term herein. Alternatively, the polybasic carboxylic acid may have hundreds or thousands of ionizable carboxylate groups per molecule; for example, hyaluronan, also known as hyaluronic acid, which is an acidic polysaccharide, is a polybasic carboxylic acid within the meaning assigned herein. The hyaluronan or hyaluronic acid may be in an ionized or salt form within the meaning used herein. Thus sodium hyaluronate is a polybasic carboxylic acid within the meaning of the term as used herein. An example of the chemical structure of a segment of a hyaluronan polymer is shown in FIG. 2.

As used herein, the term "acidic polysaccharide" refers to polymeric carbohydrates comprising carboxylic acid groups. The polymeric carbohydrate can be naturally occurring, or can be synthetic or semi-synthetic. Examples of acidic polysaccharides are hyaluronan and carboxymethyl cellulose. Carboxymethylcellulose, as is well-known in the art, is prepared by reaction of cellulose with sodium chloroacetate, and the product is believed to contain acidic carboxymethyl groups covalently linked to the primary hydroxyl groups of the anhydroglucose monomeric units that make up the cellulose molecule. An oxidized hyaluronan, that is, hyaluronan that has been treated with an oxidizing agent, such as sodium periodate, that cleaves vicinal diol moieties and provides aldehyde groups, is an acidic polysaccharide within the meaning herein, and is also an oxidized polysaccharide within the meaning herein.

The term "oxidized polysaccharide" refers to a polymeric carbohydrate, acidic or non-acidic, that has undergone treatment with an oxidizing reagent, such as sodium periodate, that cleaves vicinal diol moieties of the carbohydrate to yield aldehyde groups. An oxidized hyaluronan, that is, hyaluronan that has been treated with an oxidizing agent, such as sodium periodate, that cleaves vicinal diol moieties and provides aldehyde groups, is an example of an acidic polysaccharide within the meaning herein. An oxidized dextran, that is, dextran that has been treated with an oxidizing agent, such as sodium periodate, that cleaves vicinal diol moieties and provides aldehyde groups, is another example of an oxidized polysaccharide within the meaning herein. Another example of an oxidized polysaccharide is an oxidized starch, that is, a starch that has been treated with an oxidizing agent, such as sodium periodate, that provides aldehyde groups. It is believed that the aldehyde groups of oxidized polysaccharides interact with the amino groups of an alkylated chitosan in such a way as to markedly increase the viscosity of the mixture and cause gelation. While not wishing to be bound by theory, it is believed that this intermolecular interaction takes place through the formation of imines, or Schiff bases, between the amino groups and the aldehyde groups.

A "dehydrating reagent" as used herein refers to a molecular species that takes up the elements of water from a reaction, serving to drive a coupling reaction by thermodynamic factors. A dehydrating reagent is an compound that undergoes reaction of covalent bonds upon taking up the elements of water, as opposed to merely absorbing water into physical particles or the like. Preferably a dehydrating reagent is an organic compound. A specific example of a dehydrating reagent is a carbodiimide, that takes up the elements of water and undergoes changes in covalent bonds to ultimately yield a urea derivative.

As used herein, a "carbodiimide" is a class of organic substances comprising a R—N═C═N—R' moiety. The R and R' groups may be any organic radicals. For example, when R and R' are cyclohexyl groups, the carbodiimide is 1,3-dicyclohexylcarbodiimide, a dehydrating reagent well known in the art. A water-soluble carbodiimide is a carbodiimide that has sufficient solubility in water to form a homogeneous solution at concentrations suitable to carry out the gelation reaction as described herein. Typically, a water-soluble carbodiimide contains an ionic group, such as an ammonium salt, to confer water-solubility upon the molecule. The water-soluble diimide EDCI is 1-ethyl-3-N,N-dimethylaminopropylcarbodiimide.

A "carboxyl activating reagent" as used herein refers to a molecular species that interacts with a carboxyl group in such a way as to render the carbonyl of the carboxyl group more susceptible to nucleophilic attack, as by an amine to yield an amide. This activation may take place by formation of a complex or by formation of a covalent intermediate. A specific example of a carboxyl activating reagent is an N-hydroxy compound that can form an N-hydroxy ester of the carboxylic acid group, increasing the reactivity of the carbonyl moiety to nucleophilic addition of a molecular species such as an amine.

The term "N-hydroxy compound" refers to an organic compound comprising a chemical bond between a hydroxyl group and a nitrogen atom. Specific N-hydroxy compounds such as N-hydroxysuccinimide and N-hydroxybenztriazole (1-hydroxy benzotriazole) are well known in the art as reagents that form esters with carboxylic acid groups and serve to activate the carboxylic acid group in reactions with nucleophiles.

"Gelatin," as the term is used herein, is a collagen-derived material that is about 98-99% protein by dry weight. The approximate amino acid composition of gelatin is: glycine 21%, proline 12%, hydroxyproline 12%, glutamate 10%, alanine 9%, arginine 8%, aspartate 6%, lysine 4%, serine 4%, leucine 3%, valine 2%, phenylalanine 2%, threonine 2%, isoleucine 1%, hydroxylysine 1%, methionine and histidine <1% and tyrosine <0.5%.

An "aqueous medium," as the term is used herein, refers to a liquid medium composed largely, but not necessarily exclusively, of water. Other components may also be present, such as salts, co-solvents, buffers, stabilizers, dispersants, colorants and the like.

As used herein, the act of "mixing between mutually coupled syringes" refers to a procedure wherein one syringe is partially filled with one ingredient, a second syringe is partially filled with a second ingredient, and the two syringes are coupled together as with a luer connector such that the contents of the syringes are mixed by drawing the contents of one syringe through the connector into the second syringe, then reciprocally expelling the contents of the second syringe back into the first syringe. This process may be repeated until adequate mixing is achieved.

A "suture" or the act of "suturing" refers to the physical joining of two separate masses of tissue with thread or fiber, or alternatively with solid materials such as fabrics or plastic films on which an adhesive is disposed, whereby the physical joining serves to hold the separate tissue masses in close physical proximity at least temporarily, such as for the period of time required for biological healing to occur. A "suture line" is a line of, for example, stitches of thread as is used to close an incision at the end of a surgical procedure.

A "therapeutic agent" is any agent which serves to repair damage to a living organism to heal the organism, to cure a malcondition, to combat an infection by a microorganism or a virus, to assist the body of the living mammal to return to a healthy state. A "protective agent" is any agent which serves to prevent the occurrence of damage to an organism, such as by preventing the establishment of an infection by a microorganism, to prevent the establishment of a malcondition, to preserve an otherwise healthy body in the state of health. Therapeutic and protective agents comprise pharmaceuticals, radiopharmaceuticals, hormones or their analogs, enzymes, materials for genetic therapy such as antisense nucleotides or their analogs, macroscopic ingredients such as bone powder as is used to induce bone growth, growth factors as may be used to stimulate tissue growth such as by angiogenesis, or any other such agents as are medically advantageous for use to treat a pathological condition. As used herein, "treating" or "treat" includes (i) preventing a pathologic condition from occurring (e.g. prophylaxis); (ii) inhibiting the pathologic condition or arresting its development; (iii) relieving the pathologic condition; and/or (iv) diminishing symptoms associated with the pathologic condition.

A therapeutic agent or a protective agent may comprise a "drug." As used herein, a "drug" refers to a therapeutic agent or a diagnostic agent and includes any substance, other than food, used in the prevention, diagnosis, alleviation, treatment, or cure of a disease. Stedman's Medical Dictionary, $25^{th}$ Edition (1990). The drug can include any substance disclosed in at least one of: The Merck Index, $12^{th}$ Edition (1996); Pei-Show Juo, Concise Dictionary of Biomedicine and Molecular Biology, (1996); U.S. Pharmacopeia Dictionary, 2000 Edition; and Physician's Desk Reference, 2001 Edition.

Specifically, the drug can include, but is not limited to, one or more polynucleotides, polypeptides, oligonucleotides, gene therapy agents, nucleotide analogs, nucleoside analogs, polynucleic acid decoys, therapeutic antibodies, anti-inflammatory agents, blood modifiers, anti-platelet agents, anti-coagulation agents, immune suppressive agents, anti-neoplastic agents, anti-cancer agents, anti-cell proliferation agents, and nitric oxide releasing agents.

The polynucleotide can include deoxyribonucleic acid (DNA), ribonucleic acid (RNA), double stranded DNA, double stranded RNA, duplex DNA/RNA, antisense polynucleotides, functional RNA or a combination thereof. In one embodiment, the polynucleotide can be RNA. In another embodiment, the polynucleotide can be DNA. In another embodiment, the polynucleotide can be an antisense polynucleotide.

The polynucleotide can be a single-stranded polynucleotide or a double-stranded polynucleotide. The polynucleotide can have any suitable length. Specifically, the polynucleotide can be about 2 to about 5,000 nucleotides in length, inclusive; about 2 to about 1000 nucleotides in length, inclusive; about 2 to about 100 nucleotides in length, inclusive; or about 2 to about 10 nucleotides in length, inclusive.

An antisense polynucleotide is typically a polynucleotide that is complimentary to an mRNA, which encodes a target protein. For example, the mRNA can encode a cancer promoting protein i.e., the product of an oncogene. The antisense polynucleotide is complimentary to the single stranded mRNA and will form a duplex and thereby inhibit expression of the target gene, i.e., will inhibit expression of the oncogene. The antisense polynucleotides of the invention can form a duplex with the mRNA encoding a target protein and will disallow expression of the target protein.

A "gene therapy agent" refers to an agent that causes expression of a gene product in a target cell through introduction of a gene into the target cell followed by expression. An example of such a gene therapy agent would be a genetic construct that causes expression of a protein, such as insulin, when introduced into a cell. Alternatively, a gene therapy agent can decrease expression of a gene in a target cell. An example of such a gene therapy agent would be the introduction of a polynucleic acid segment into a cell that would integrate into a target gene and disrupt expression of the gene. Examples of such agents include viruses and polynucleotides that are able to disrupt a gene through homologous recombination. Methods of introducing and disrupting genes within cells are well known to those of skill in the art.

Nucleotide and nucleoside analogues are well known on the art. Examples of such nucleoside analogs include, but are not limited to, Cytovene® (Roche Laboratories), Epivir® (Glaxo Wellcome), Gemzar® (Lilly), Hivid® (Roche Laboratories), Rebetron® (Schering), Videx® (Bristol-Myers Squibb), Zerit® (Bristol-Myers Squibb), and Zovirax® (Glaxo Wellcome). See, Physician's Desk Reference, 2001 Edition.

As used herein, a "peptide" and a "protein" refer to polypeptides, linear polymers of amino acids, the difference between the terms "peptide" and "protein" largely being in the length of the polymer. In one embodiment, the polypeptide can be an antibody. Examples of such antibodies include single-chain antibodies, chimeric antibodies, monoclonal antibodies, polyclonal antibodies, antibody fragments, Fab fragments, IgA, IgG, IgM, IgD, IgE and humanized antibodies. In one embodiment, the antibody can bind to a cell adhesion molecule, such as a cadherin, integrin or selectin. In another embodiment, the antibody can bind to an extracellular matrix molecule, such as collagen, elastin, fibronectin or laminin. In still another embodiment, the antibody can bind to a receptor, such as an adrenergic receptor, B-cell receptor, complement receptor, cholinergic receptor, estrogen receptor, insulin receptor, low-density lipoprotein receptor, growth factor receptor or T-cell receptor. Antibodies of the invention can also bind to platelet aggregation factors (e.g., fibrinogen), cell proliferation factors (e.g., growth factors and cytokines), and blood clotting factors (e.g., fibrinogen). In another embodiment, an antibody can be conjugated to an active agent, such as a toxin or a radionuclide.

An "anti-cancer agent" means an agent that either inhibits the growth of cancerous cells, or causes the death of cancerous cells. Anti-cancer agents include, e.g., nucleotide and nucleoside analogs, such as 2-chloro-deoxyadenosine, adjunct antineoplastic agents, alkylating agents, nitrogen mustards, nitrosoureas, antibiotics, antimetabolites, hormonal agonists/antagonists, androgens, antiandrogens, antiestrogens, estrogen & nitrogen mustard combinations, gonadotropin releasing hotmone (GNRH) analogues, progestrins, immunomodulators, miscellaneous antineoplastics, photosensitizing agents, and skin & mucous membrane agents. See, Physician's Desk Reference, 2001 Edition.

An "antimicrobial," as used herein, refers to a molecular entity that is effective as a therapeutic agent or as a protective agent against an infection by a microorganism, which could be a bacterium, a protozoan, a fungus, a virus, or another pathogenic living organism. An antimicrobial may be an antibiotic, effective against bacteria, including aminoglycoside antibiotics such as gentamicin or streptomycin, a cephalosporin such as cephalexin or cephtriaxone, a carbacephem such as loracarbef, a glycopeptide such as vancomycin, a macrolide such as erythromycin, a penicillin such as amoxicillin or ampicillin, a polypeptide such as bacitracin or polymyxin B, a quinolone such as ciprofloxacin, a tetracycline such as oxytetracycline, a sulfonamide, or any other medically approved agent for treatment of bacterial infections. Alternatively the antimicrobial may be an antifungal agent such as ketoconazole, miconazole or amphotericin B, or an antiviral agent such as acyclovir or AZT.

A "radioactive material" as used herein refers to any naturally occurring or manmade substance that emits ionizing radiation such as gamma rays, beta particles, Auger electrons, X-rays, or alpha particles. A radioactive material may be used for diagnostic purposes, such as for imaging as in positron emission tomography (PET). A radionuclide commonly used for imaging diagnostics is fluorine-18. Alternatively a radioactive material may be used for therapeutic purposes, as in treating tumors. Radionuclides used therapeutically include technetium-99m, iodine-123 and -131, and gallium-67, among others.

In the claims provided herein, the steps specified to be taken in a claimed method or process may be carried out in any order without departing from the principles of the invention, except when a temporal or operational sequence is explicitly defined by claim language. Recitation in a claim to the effect that first a step is performed then several other steps are performed shall be taken to mean that the first step is performed before any of the other steps, but the other steps may be performed in any sequence unless a sequence is further specified within the other steps. For example, claim elements that recite "first A, then B, C, and D, and lastly E" shall be construed to mean step A must be first, step E must be last, but steps B, C, and D may be carried out in any sequence between steps A and E and the process of that sequence will still fall within the four corners of the claim.

Furthermore, in the claims provided herein, specified steps may be carried out concurrently unless explicit claim language requires that they be carried out separately or as parts of different processing operations. For example, a claimed step of doing X and a claimed step of doing Y may be conducted simultaneously within a single operation, and the resulting process will be covered by the claim. Thus, a step of doing X, a step of doing Y, and a step of doing Z may be conducted simultaneously within a single process step, or in two separate process steps, or in three separate process steps, and that process will still fall within the four corners of a claim that recites those three steps.

Similarly, except as explicitly required by claim language, a single substance or component may meet more than a single functional requirement, provided that the single substance fulfills the more than one functional requirement as specified by claim language.

DETAILED DESCRIPTION

A hydrogel for use as a tissue sealant according to the present invention is a hydrogel that achieves a gelled state after formation from a premix composed of more than a single component. The hydrogel, which may be used to seal the tissues of a living mammal such as a human patient, is formed upon gelation of the premix, which is in the physical form of a sol. Mixing of the components that make up the premix provides a liquid or semi-liquid sol that may be pumped or transferred by any technique suitable for handling somewhat viscous liquid materials, such as syringes, pipettes, tubing and the like. Upon standing, the premix sol after a period of time sets up into the hydrogel of the present invention.

The premix sol and the resulting hydrogel that forms from the sol are suitable for contact with living biological tissue, being biocompatible and preferably biodegradable. Thus, the hydrogel can remain in contact with living biological tissue within a human patient for an extended period of time without damaging the tissue on which it is disposed. In one specific embodiment, the hydrogel has adhesive properties towards living tissues on which it is disposed. In another specific embodiment, the hydrogel contains therapeutic or protective agents that are released into the surrounding tissues on which the hydrogel is disposed. In another specific embodiment, the hydrogel has both adhesive properties towards the tissue on which it is disposed and also contains therapeutic or protective agents that are released into the surrounding tissues on which the hydrogel is disposed. In another specific embodiment the hydrogel contains microspheres or nanospheres containing therapeutic agents or protective agents that further control the release of the agents from the hydrogel.

A specific embodiment of a premix that forms a hydrogel according to the present invention comprises an alkylated chitosan. Referring to FIG. 1, in a specific embodiment an alkylated chitosan comprises a poly(oxyethylene)chitosan. The poly(oxyethylene)chitosan is a polymer formed of 2-amino-2-deoxyglucose monomeric units. Each monomeric unit comprises a single free amino group and two free hydroxyl groups. In FIG. 1, one amino group is alkylated on the nitrogen atom with a poly(oxyethylene) chain, also known as a polyethyleneglycol chain. In the example provided in FIG. 1, the chitosan has a degree of substitution of 0.5, because two of the four amino groups in the tetrameric unit shown bears the substituent. However, a poly(oxyethylene)chitosan according to the present invention may have a degree of amino group substitution ranging down to about 0.1 (wherein only one in about every ten monomeric units is alkylated). Furthermore, a poly(oxyethylene)chitosan according to the present invention may also bear the poly(oxyethylene) derivative on one of the two free hydroxyl groups in a given monomeric unit, or may comprises a mixture of N- and O-alkylated chitosan monomeric units, or be di-alkylated or tri-alkylated on a single monomer unit. Thus, a fully alkylated chitosan monomeric unit has a degree of substitution of 3.0, and a poly(oxyethylene)chitosan according to the present invention may have a degree of substitution ranging up to 3.0 without departing from the principles of the invention.

A preferred degree of substitution for a poly(oxyethylene) chitosan is about 0.35 to about 0.95. A particularly preferred degree of substitution is about 0.5.

It should be understood that other poly(oxyalkylene) groups may be substituted for the poly(oxyethylene) group shown in FIG. 1. For example, a poly(oxypropylene)chitosan may be used in place of, or in addition to, the poly(oxyethylene)chitosan. A poly(oxypropylene) group is the structure that would be obtained if the poly(oxyethylene) group as shown in FIG. 1 bore a methyl group on every ethylene unit (—O—CH$_2$CH(CH$_3$)—O), or alternatively, every ethylene unit shown in FIG. 1 were a 3-carbon linear propylene group (—O—CH$_2$CH$_2$CH$_2$—O—).

The number of monomeric units that make up a chitosan according to the present invention may vary widely without departing from the principles of the invention. Any sample that contains more than a single molecule of a chitosan derivative will almost inevitably contain a distribution of molecules of different molecular weights. A preferred poly(oxyethylene)chitosan according to the present invention has a molecular weight of about 200 kD to about 600 kD.

In a specific embodiment, a premix for a hydrogel contains a polybasic carboxylic acid comprising a hyaluronan. A member of the class of acidic polysaccharides, a hyaluronan bears an ionizable carboxylic acid group on every other monosaccharide residue. The hyaluronan can be in the form of a hyaluronate, that is, with at least most of the carboxylic acid groups being in the ionized or salt form. Sodium hyaluronate is a specific example. Referring to FIG. 2, a hyaluronan or a hyaluronic acid is a polybasic carboxylic acid, and the number of ionizable carboxylate groups per hyaluronan molecule is dependent on the degree of polymerization of the hyaluronan. The degree of substitution of carboxylic acid groups on the polymer backbone, assuming a monomeric unit comprising the disaccharide formed of one glucuronic acid monosaccharide and one 2-acetamido-2-deoxyglucose monosaccharide, is 1.0. Every monomeric unit (disaccharide unit) bears a single ionizable carboxylic acid group. A hyaluronan may be of any of a wide range of degrees of polymerization (molecular weights), but a preferred hyaluronan has a molecular weight of about 2,000 kD to about 3,000 kD. An example of a premix comprising a hyaluronan further comprises a poly(oxyethylene)chitosan, synonymously a PEG-chitosan.

Another specific embodiment of a premix that forms a hydrogel according to the present invention comprises an acrylated chitosan. Referring to FIG. 4, in a specific embodiment an alkylated chitosan comprises a acrylated chitosan wherein at least some of the free amino groups of the 2-amino-2-deoxyglycose monosaccharide monomeric units are substituted with acrylate groups. It is believed that acrylate groups are bonded to free amino groups of the chitosan via a Michael type conjugate addition wherein the nucleophilic amino group forms a bond to the β-carbon of the α,β-unsaturated acrylate, but the acrylate may be bonded to the chitosan in a different manner without departing from the principles of the invention. Furthermore, as is illustrated in FIG. 4, acrylates may themselves oligomerize after initial alkylation of the chitosan backbone. The three-carbon carboxylic acid substituent on the left illustrates the alkylation of chitosan with a single molecule of acrylate, whereas the six-carbon dicarboxylic acid substituent on the right illustrates the product resulting from addition of a second acrylate molecule to the first acrylate molecule, either prior to or subsequent to addition of the first acrylate molecule to the chitosan backbone.

A preferred degree of substitution of the chitosan backbone with acrylate groups according to the present invention is about 0.25 to about 0.45. The number of monomeric units that make up a acrylated chitosan according to the present invention may vary widely without departing from the principles of the invention. Any sample that contains more than a single molecule of a chitosan derivative will almost inevitably contain a distribution of molecules of different molecular weights. A preferred acrylated chitosan has a molecular weight of about 200 kD to about 600 kD.

Figure 5:
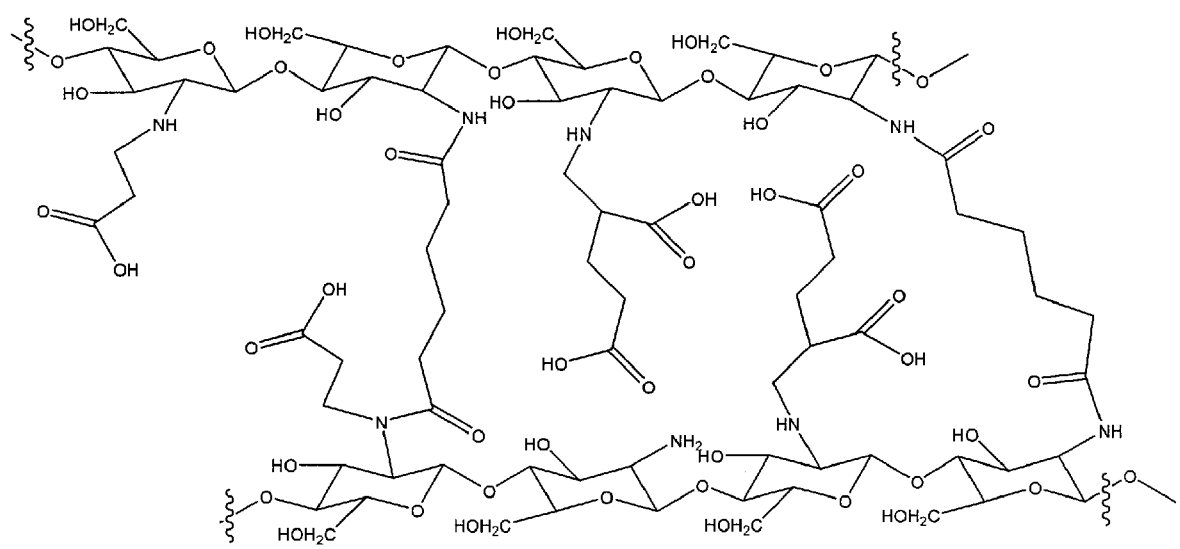
FIG. 5 shows a segment of the acrylated chitosan polymer of FIG. 4 crosslinked by amide linkages formed with a adipic acid.

A premix that includes an acrylated chitosan can also include a polybasic carboxylic acid comprising a dicarboxylic acid. A preferred dicarboxylic acid is a dicarboxylic acid wherein the two carboxylate groups are bonded to a moiety of about one to about twelve carbon atoms, which may comprise chains, aliphatic or aromatic rings, or heteroatoms such as nitrogen, oxygen or sulfur. Referring to FIG. 5, a particularly preferred dicarboxylic acid is a linear alkyl α,ω-dicarboxylic acid, which can crosslink acrylated chitosan polymer chains through the intermolecular formation of amide bonds between the chitosan amino groups and the carboxylic acid groups of the dicarboxylic acid. Specific examples of linear alkyl α,ω-dicarboxylic acids are malonic, succinic, glutaric, adipic, pimelic, suberic, azaleic, and sebacic acid. A particularly preferred example is adipic acid. A specific example of a premix of the invention comprises acrylated chitosan, disodium adipate, a dehydrating reagent and a carboxyl activating reagent.

In another specific embodiment, a premix that includes an alkylated chitosan also includes a polybasic carboxylic acid comprising a carboxymethylcellulose. A carboxymethylcellulose is a derivative of cellulose (a β-1,4 linked polymer of glucose) wherein hydroxyl groups are substituted with carboxymethyl (—$CH_2CO_2H$) moieties. It is understood that the term carboxymethylcellulose comprises salts of carboxymethylcellulose, such as the sodium salt. A specific example of a premix comprises acrylated chitosan, carboxymethylcellulose sodium salt, a dehydrating reagent and a carboxyl activating reagent. Carboxymethylcellulose, as is well-known in the art, may have varying degrees of substitution, a "degree of substitution" referring to the number of derivatizing groups, herein carboxymethyl, per each monomer unit on the average. A particularly preferred carboxymethylcellulose according to the present invention has a degree of substitution of about 0.7 and a molecular weight of about 80 kD.

A premix according to the present invention comprises an aqueous medium. An aqueous medium necessarily includes water, and may include other components including salts, buffers, co-solvents, additional cross-linking reagents, emulsifiers, dispersants, electrolytes, or the like.

A premix according to the present invention can comprise a dehydrating reagent. A preferred dehydrating reagent is a dehydrating reagent that is sufficiently stable when dissolved or dispersed in an aqueous medium to assist in driving the formation of the amide bonds before it is hydrolyzed by the water in the aqueous medium. A particularly preferred type of dehydrating reagent is a carbodiimide, which is transformed to a urea compound through incorporation of the elements of water. An example of a water-soluble carbodiimide, is 1-ethyl-3-(N,N-dimethylpropyl)carbodiimide (EDCI), which is preferred as it is soluble in the aqueous medium and thus does not require a co-solvent or dispersant to distribute it homogeneously throughout the premix. Other water-soluble carbodiimides are also preferred dehydrating reagents.

A premix according to the present invention can comprise a carboxyl activating reagent. A preferred carboxyl activating reagent is a reagent that serves to activate a carboxyl group towards formation of a new bond, such as an amide or ester bond with an amine or a hydroxyl-bearing compound respectively. A specific embodiment of a carboxyl activating reagent reacts with the carboxyl group to form a new compound as an intermediate, which then further reacts with another substance such as an amine to form an amide, or a hydroxyl-bearing compound to form an ester. A preferred carboxyl activating reagent is an N-hydroxy compound. An N-hydroxy compound reacts with a carboxyl group to form an N-hydroxy ester of the carboxylic acid, which may subsequently react with, for example, an amino group to form an amide. An example of an N-hydroxy compound is N-hydroxysuccinimide. Another example of an N-hydroxy compound is N(1)-hydroxybenzotriazole.

Another preferred carboxyl activating reagent is a carbodiimide. A carbodiimide reacts with a carboxyl group to form an O-acylisourea, which may subsequently react with, for example, an amine to form an amide, releasing the carbodiimide transformed through covalent addition of the elements of water to a urea compound. A preferred carbodiimide is a water-soluble carbodiimide, for example EDCI.

In a specific embodiment of the present invention, a carbodiimide may serve both as a dehydrating reagent and as a carboxyl activating reagent. Thus, a premix comprising an alkylated chitosan, a polybasic carboxylic acid, and a carbodiimide is a specific embodiment according to the present invention. Another specific embodiment is a premix comprising an alkylated chitosan, a polybasic carboxylic acid, a carbodiimide, and another molecular species wherein that species is a carboxyl activating reagent. Another specific embodiment is a premix comprising an alkylated chitosan, a polybasic carboxylic acid, a carbodiimide, and another molecular species wherein that species is a dehydrating reagent.

In an embodiment of a composition of the invention, an alkylated chitosan forms a hydrogel after mixing with an oxidized polysaccharide in an aqueous medium. The initial sol formed after mixing undergoes gelation over a period of time, typically a few minutes, to provide a hydrogel of the invention. A specific example of an oxidized polysaccharide is oxidized dextran. Additional examples are oxidized starch and oxidized hyaluronan. A specific composition of the invention comprises acrylated chitosan and oxidized dextran, which readily forms a hydrogel without addition of a dehydrating reagent or of a carboxyl activating reagent.

Upon standing at room temperature or at the temperature of the human body, a premix sol of the invention, after a period of time that is typically in the order of a few minutes, for example about 0.5 minutes to about 20 minutes at about 37° C., or about 1 minute to about 10 minutes at about 37° C., undergoes gelation to form a hydrogel of the invention. A premix sol and a resulting hydrogel that forms from the sol are suitable for contact with living biological tissue, being biocompatible and preferably biodegradable. Thus, the hydrogel can remain in contact with living biological tissue within a human patient for an extended period of time without damaging the tissue on which it is disposed.

In an embodiment of the invention, the hydrogel contains therapeutic or protective bioactive agents that are released into the surrounding tissues. Bioactive agents can be combined with premix solutions by simply blending commercially available solutions of polypeptides or other agents with the aqueous solutions, with gentle mixing. Cells can likewise be blended with the composition, preferably immediately prior to emplacement to enhance survival of living cells.

A radiopaque material that is optionally incorporated in the composition may be fine particles of a selected radiopaque metal, such as gold, platinum, tantalum, barium, or the like. Alternatively, a radiopaque agent can be an iodinated organic compound. A specific example is iohexol.

A variety of types of a bioactive agent can be incorporated into the composition of the invention. The agent can be a molecular entity, such as a regenerative agent such as one or more human growth modulating factors such as interleukins, transformation growth factor-b, fibroblast growth factor (FGF) or vascular endothelial growth factor (VEGF), a gene therapy agent, a cogener of platelet derived growth factor, a monoclonal antibody directed against growth factors; a drug, or a cell regeneration factor. A bioactive agent may also be a cellular entity such as a plurality of drug-producing cells or of regenerative cells such as stem cells.

In another embodiment of the invention, the hydrogel contains microspheres or nanospheres containing therapeutic agents or protective bioactive agents, the microspheres or nanospheres further controlling the release of the bioactive agents from the hydrogel into the surrounding tissues. A "microsphere" or a "nanosphere" as used herein is a particulate body of dimensions of the order of microns (micrometers) or nanometers respectively, wherein the particulate body may be hollow or solid. Microspheres and nanospheres may be formed of organic or inorganic materials. For example, a nanosphere may comprise a buckminsterfullerene (buckyball), which is organic. Alternatively a nanosphere may comprise microporous glass, which is inorganic. It is understood that the terms encompass solid lipid nanoparticles, wherein the nanosphere particles are formed from a solid lipid. Preferably the microsphere or the nanosphere contains a drug or other substance, the timing of the release of which it is advantageous to control.

Due to the abundance of cationic amino groups in the chitosan structure, it is known that drugs with carboxyl groups can been conjugated thereto and sustained release can be achieved through the hydrolysis of the amide or ester bonds linking drugs to the chitosan molecule. Y. D. Sanzgiri, et al., Pharm. Res., 1, 418 (1990). As a polyelectrolyte, chitosan can also electrostatically conjugate sensitive bioactive agents while preserving their bioactivities and enhancing their stabilities. Such derivatives may be formed with the acrylated chitosan of the present invention, and will likewise serve to provide for sustained release and to preserve the bioactivity and to enhance the stability of the conjugated agent(s).

The abundance of positive charges on the alkylated chitosan enables the electrostatic binding of biologically active proteins such as rhVEGF. This is the most gentle mode of conjugating proteins and thus protecting and preserving the bioactivity of sensitive proteins like rhVEGF. The conjugation of proteins like rhVEGF to the alkylated chitosan also serves as a mechanism for modulating the biological activity of the growth factor, thereby limiting the potential for induction of uncontrolled tissue development.

The types of cells that may be incorporated into the composition include progenitor cells of the same type as those from the tissue site, and progenitor cells that are histologically different from those of the tissue site such as embryogenic or adult stem cells, that can act to accelerate the healing process. The therapeutic composition comprising cells can be administered in the form of a solution or a suspension of the cells mixed with the polymer solution, such that the cells are substantially immobilized within the application site upon gelation of the premix. This serves to concentrate the effect of the therapeutic agent or the cells at the site of the tissue damage and to provide for release of the agent or of the cells or of cellular products over a course of time.

A hydrogel of the invention adheres to the living tissues on which it is disposed such that it may be used as a tissue sealant. A tissue sealant of the invention has at least sufficient adhesivity such that after gelation, the hydrogel resists detachment from the tissue when subjected to a force at least as strong as may be applied when a patient moves, or by the weight of an organ acted on by gravity, or by involuntary motions of surrounding tissues (heartbeat, peristalsis, etc.). For applications where the disrupting strain is likely to be more severe, for example in a limb where voluntary muscles exert a greater force, the tissue sealant preferably adhesively seals the tissue such that it can resist a relatively large disruptive force. The hydrogel is of sufficient strength and elasticity such that the physical integrity of the mass of sealant as it is disposed on the tissue is maintained while the hydrogel adheres to the tissue. The inventive tissue sealant thus is suitable for at least temporarily holding the tissue surrounding a tear, hole, perforation, incision or any separation of tissue in physical proximity. For example, the inventive tissue sealant is adapted to seal any laceration, cut, abrasion, or disruption of dermal tissue, i.e., skin.

A specific tissue sealant of the invention also preferably seals the tear, hole, perforation or incision in order to prevent leakage of any vital bodily fluids that are normally retained by the tissue in its undamaged state. For example, the outer membrane surrounding the brain and the spinal cord, the dura mater, serves to contain the cerebrospinal fluid in which the nervous system tissue is normally immersed. A specific use for the tissue sealant according to the present invention is the repair or sealing of the dura, such as after brain surgery. To surgically reach the brain in order to carry out any of the operative procedures that may be applied within the brain to treat or cure a malcondition, an incision must be made in the dura, and when the surgical procedures within the brain are complete, it is desirable to close the dura as tightly as possible to avoid leakage of cerebrospinal fluid to areas external to the dura as well as to allow healing of the tissue. A specific tissue sealant of the present invention is well suited to provide this closure and sealing, either as a reinforcement of a suture line or without additional closure techniques being used.

In this specific use of a tissue sealant of the invention, the premix is prepared and is applied to the incision in the sol form. For aid to the surgeon in visualizing the application of the tissue sealant, the sealant may comprise a dye or a fluorescent material to better enable the surgeon to see and thus control the distribution of the sealant on the tissue being repaired. The sealant may also comprise a radio-opaque agent to aid in visualization of the disposition of the sealant post-operatively.

A specific technique for preparing the premix is with the use of two syringes coupled with a Luer coupling fitting. The fitting optionally contains a three-way T-valve. One syringe is partially filled with a solution comprising an alkylated chitosan dissolved in an aqueous medium. A second syringe is partially filled with a solution comprising a polybasic carboxylic acid dissolved in an aqueous medium. Optionally, either solution may contain additional components such as a co-solvent, dispersant, emulsifier or other additive to assist in dissolving or dispersing the polymeric component. Optionally, either syringe may further contain a dehydrating reagent, a carboxyl activating reagent or both.

Formation of the premix takes place by reciprocally exchanging the contents of the two syringes through the coupling fitting, first depressing the plunger of one syringe to expel the contents into the second syringe, then depressing the plunger of the second syringe to expel the mixed contents back into the first syringe. This procedure is preferably repeated until substantial homogeneity is achieved. Optionally a dehydrating reagent, a carboxyl activating reagent, or both, may be added by replacing the empty syringe with a third syringe charged with a solution of the reagent(s) and repeating the reciprocal exchange. Then, the charged syringe containing the homogeneous premix is attached to a suitable application tip, which is used to transfer the premix such that it is disposed on the tissue to be sealed, for example an incision in the dura mater.

In a similar manner the premix may be applied to other tissue types in need of sealing, such as dermal tissue, musculature, and so forth. For example, the premix of a tissue sealant may be applied to seal the annulus of a ruptured inter-vertebral disc as part of a surgical procedure to repair a ruptured disc.

A premix may be mixed up in any suitable container, taken up in a syringe or pipette, and transferred to the tissue to be sealed, or it may be poured onto the tissue in a controlled manner. Preferably, complete application of the premix to the tissue takes place before significant gelling occurs, although the premix may undergo a certain amount of thickening prior to application without departing from the principles of the invention.

The premix preferably gels within a relatively short time frame, but not instantly, to enable the premix to be applied to the tissue to be sealed before substantial gelling takes place. Nevertheless, the premix preferably forms the hydrogel within the timeframe of minutes, such that surgical procedures are not unduly delayed or interrupted by periods of time wherein the gelling is taking place. Preferably gelling takes place within about 1 minute to about 12 minutes at the body temperature of the patient, around 37° C. It is understood that even after the premix gels to a sufficient degree that the hydrogel ceases to be flowable, additional gelling or hardening may take place. It is preferred that gelation has occurred to a sufficient degree within the 1 to 12 minute time window to permit surgical procedures to continue. Thus, it is preferred that both gelling and adhesion of the hydrogel be sufficiently achieved in this time window that the tissue and its surroundings may be at least gently manipulated by the end of the time window without causing flow of ungelled premix or detachment of adhered hydrogel from the tissue on which the hydrogel is disposed.

The tissue sealant of the present invention preferably is dimensionally stable after gelling in the presence of aqueous media, such as in a living human body. The tissue sealant does not absorb water or swell greatly in the presence of water. This is particularly preferable when the tissue sealant is disposed in proximity to nerves, where swelling and the resulting pressure applied to the nerves is particularly disadvantageous. The dimensional stability of a tissue sealant comprising a hydrogel is an outstanding feature according to the present invention. This dimensional stability enables a tissue sealant of the present invention to be particularly well-suited for use in proximity to neural tissue, for example in sealing of dura mater in brain neurosurgery. In brain neurosurgery, avoidance of post-surgical swelling is especially critical, thus the dimensional stability of a tissue sealant of the present invention is highly advantageous in such use.

It is to be understood that while the invention has been described in conjunction with the detailed description thereof, the foregoing description is intended to illustrate and not limit the scope of the invention, which is defined by the scope of the claims. Other aspects, advantages, and modifications are within the scope of the claims and will doubtless be apparent to persons of ordinary skill in the art.

EXAMPLES

Example 1

Preparation of Acrylated Chitosan

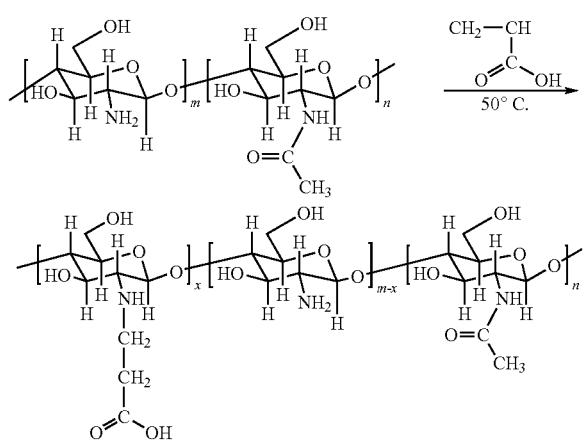

5.52 ml of acrylic acid was dissolved in 150 ml of double distilled water and 3 g of chitosan (Kraeber® 9012-76-4, molecular weight 200-600 kD) was added to it. The mixture was heated to 50 C and vigorously stirred for 3 days. After removal of insoluble fragments by centrifugation, the product was collected and its pH was adjusted to 11 by adding NaOH solution. The mixture was dialyzed extensively to remove impurities.

Example 2

Preparation of PEG-Chitosan

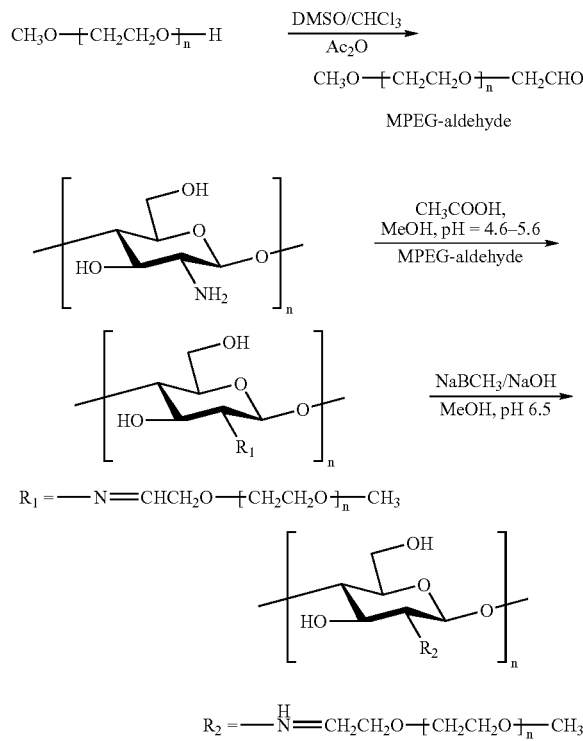

Monomethyl-PEG-aldehyde was prepared by the oxidation of Monomethyl-PEG (MPEG) with DMSO/acetic anhydride: 10 g of the dried MPEG was dissolved in anhydrous DMSO (30 ml) and chloroform (2 ml). Acetic anhydride (5 ml) was introduced into the solution and the mixture is stirred for 9 h at room temperature. The product was precipitated in 500 ml ethyl ether and filtered. Then the product was dissolved in chloroform and re-precipitated in ethyl ether twice and dried.

Chitosan (0.5 g, 3 mmol as monosaccharide residue containing 2.5 mmol amino groups, Kraeber 9012-76-4, molecular weight 200-600 kD) was dissolved in 2% aqueous acetic acid solution (20 ml) and methanol (10 ml). A 15 ml sample of MPEG-aldehyde (8 g, DC: 0.40) in aqueous solution was added into the chitosan solution and stirred for 1 h at room temperature. Then the pH of chitosan/MPEG-monoaldehyde solution was adjusted to 6.0-6.5 with aqueous 1 M NaOH solution and stirred for 2 h at room temperature. NaCNBH$_3$ (0.476 g, 7.6 mmol) in 7 ml water was added to the reaction mixture dropwise and the solution was stirred for 18 h at room temperature. The mixture was dialyzed with dialysis membrane (COMW 6000-8000) against aqueous 0.5 M NaOH solution and water alternately. When the pH of outer solution reached 7.5, the inner solution was centrifuged at 5,000 rpm for 20 min. The precipitate was removed. The supernatant was freeze-dried and washed with 100 ml acetone to get rid of unreacted MPEG. After vacuum drying, the final product (white powder) was obtained as water soluble or organic solvent soluble PEG-g-Chitosan. The yield of water soluble derivatives was around 90% based on the weight of starting chitosan and PEG-aldehyde.

Example 3

Preparation of a PEG-Chitosan and Hyaluronan Hydrogel

Hyaluronan (sodium hyaluronate, Kraeber 9067-32-7) was dissolved in water as a 0.5% solution by weight. PEG-chitosan, prepared as described in Example 2, was dissolved in water as a 5% solution by weight. A sample of each solution (0.5 mL of each) was mixed, then a solution of EDCI (20 μL of a solution in water at 350 mg/mL) was added and the solution was thoroughly mixed. Immediately a solution of N-hydroxysuccinimide (20 μL of a solution in water at 125 mg/mL) was added and thoroughly mixed in to form a premix. The premix gelled into a hydrogel in about 7 minutes at ambient temperature (22° C.). At 37° C. gelation occurred in about 2 minutes.

Example 4

Preparation of a Acrylated Chitosan and Adipic Acid Hydrogel

A sample of acrylated chitosan prepared as described in Example 1 was dissolved in water at a concentration of 2% by weight. A sample of this solution (0.5 mL) was mixed with a solution of adipic acid in water (40 μL of a 20 mg/mL solution), then a solution of EDCI (20 μL of a 350 mg/mL solution) and the solution thoroughly mixed. Then, a solution of N-hydroxysuccinimide in water (20 μL of a 125 mg/mL solution) was mixed in. The premix gelled in about 9 minutes at ambient temperature (22° C.). At 37° C. gelation occurred in about 3 minutes.

Example 5

Preparation of an Acrylated Chitosan and Carboxymethylcellulose Hydrogel

A sample of acrylated chitosan prepared as described in Example 1 was dissolved in water at a concentration of 2% by weight. A sample of carboxymethylcellulose sodium salt (Polysciences no. 06140, MW 80 kD, degree of substitution 0.7) was dissolved in water at a concentration of 5% by weight. These two solutions (0.25 mL each) were mixed with a solution of EDCI (20 μL of a 6.5% solution) and the solution thoroughly mixed. Then, a solution of N-hydroxysuccinimide in water (20 μL of a 35% solution) was mixed in. The solution gelled in about 10 minutes at ambient temperature (22° C.).

Example 6

Preparation of Oxidized Dextran

Dextran (5 g) was dissolved in 400 mL of distilled H$_2$O, then 3.28 g of NaIO$_4$ dissolved in 100 mL ddH$_2$O was added. The mixture was stirred at 25° C. for 24 hrs. 10 ml of ethylene glycol was added to neutralize the unreacted periodate following by stirring at room temperature for an additional hour. The final product was dialyzed exhaustively for 3 days against doubly distilled H$_2$O, then lyophilized to obtain a sample of pure oxidized dextran.

Example 7

Analyses of Oxidized Dextran

The degree of oxidation of the oxidized dextran was determined by quantifying the aldehyde groups formed using t-butyl carbazate titration via carbazone formation. A solution of oxidized dextran (10 mg/ml in pH 5.2 acetate buffer) was prepared; and a 5-fold excess tert-butyl carbazate in the same buffer was added and allowed to react for 24 hrs at ambient temperature, then a 5-fold excess of $NaBH_3CN$ was added. After 12 hrs, the reaction product was precipitated three times with acetone and the final precipitate was dialyzed thoroughly against water, followed by lyophilization. The degree of oxidation (i.e., abundance of aldehyde groups) was assessed using $^1H$ NMR by integrating the peaks: 7.9 ppm (proton attached to tert-butyl) and 4.9 ppm (anomeric proton of dextran).

Example 8

Preparation of an Oxidized Dextran/Acrylated Chitosan Gel

A 1 mL sample of a 1-3% aqueous oxidized dextran in water solution was mixed with 1 mL of a 1-3% aqueous acrylated chitosan solution. The mixture was gently stirred for 10 seconds. Gelation occurred within 30 seconds to 10 minutes at temperatures ranging from 5° C. to 37° C.

Example 9

Preparation of Oxidized Hyaluronan

Sodium hyaluronate (1.0 gram) was dissolved in 80 ml of water in a flask shaded by aluminum foil, and sodium periodate (various amounts) dissolved in 20 ml water was added dropwise to obtain oxidized hyaluronan (oHA) with different oxidation degrees. The reaction mixture was incubated at ambient temperature and 10 ml of ethylene glycol was added to neutralize the unreacted periodate following by stirring at room temperature for an additional hour. The solution containing the oxidized hyaluronan was dialyzed exhaustively for 3 days against water, then lyophilized to obtain pure product (yield: 50-67%).

Example 10

Analyses of Oxidized Hyaluronan

The degree of oxidation of oxidized hyaluronan was determined by quantifying aldehyde groups formed with t-butyl carbazate titration via carbazone formation. A solution of the oxidized hyaluronan (10 mg/ml in pH 5.2 acetate buffer) and a 5-fold excess tertbutyl carbazate in the same buffer were allowed to react for 24 hrs at ambient temperature, followed by the addition of a 5-fold excess of $NaBH_3CN$. After 12 hrs, the reaction product was precipitated three times with acetone and the final precipitate was dialyzed thoroughly against water, followed by lyophilization. The degree of oxidation (i.e., abundance of aldehyde groups) was assessed using $^1H$ NMR by integrating the peaks: 1.32 ppm (tert-butyl) and 1.9 ppm ($CH_3$ of hyaluronic acid).

Example 11

Preparation of a PEG-Chitosan/Hyaluronan Hydrogels

A solution of PEG-chitosan (2.5 wt %) and hyaluronan (0.5%) in water at pH in the range of about 3.5 to about 5.5 was made up by first making solutions of the two polymers independently at the stated pH, then mixing the solutions. The mixture rapidly formed a viscous solution.

A solution of PEG-chitosan (1.3% w/v, 25 g), hyaluronan (2% w/v, 2.3 g), and 0.1 M HCl (pH 1.45, 0.45 g) was made up. The viscosity increased markedly within about 30 seconds. The pH of the resulting mixture was within the 3.5 to 5.5 range.

Example 12

Preparation of a Gelatin/Oxidized Hyaluronan Hydrogel

A 20% w/v solution of gelatin in water (1 ml) was mixed with a 20% solution of partially oxidized Hyaluronan (1 ml) (20.3% oxidized). The solution was warmed to about 40-45° C., above the melting point of the gelatin, and was mixed. At about 37° C. gelation occurs in about 15 minutes. Optionally, a buffer system of 0.1 M borax at pH 9.4 may be used.

Example 13

Application of a Premix to Canine Pericardium In Vitro

A premix comprising an alkylated chitosan, a polybasic carboxylic acid, a dehydrating reagent and a carboxyl activating reagent in water was made up using two syringes joined by a Luer connector. The somewhat viscous but flowable composition was then applied to a square (about 5×5 cm) of damp canine pericardium in which an incision had previously been made. The clear viscous liquid was allowed to stand in place for several minutes. A hydrogel formed and adhered to the tissue such that the pericardium square could be picked up, manipulated and stretched, showing that a clear, elastic hydrogel had sealed the incision. The hydrogel was probed with blunt forceps tips but did not rupture or detach from the surrounding tissue.

Example 14

PEG-Chitosan/Hyaluronan Hydrogel Adhesion to Murine Muscle

A premix formed as in Example 13 was disposed on the muscle tissue of a dead mouse. A hydrogel was completely formed after about 10 minutes. A moderate amount of force applied with a pair of forceps did not either detach the hydrogel from the muscle, or rupture the hydrogel. A high degree of hydrogel elasticity was observed.

Example 15

PEG-Chitosan/Hyaluronan Hydrogel Sealing of Full-Thickness Dermal Wounds in Mouse In Vivo A wound completely penetrating the thickness of the dermal layer of a living mouse was provided. A premix prepared as in Example 13 was disposed in the wound. After one week, the hydrogel was observed to be in place and detachment had not occurred. Evidence of healing along the original wound bed was observed.

Example 16

Evaluation of PEG-Chitosan/Hyaluronan Hydrogel Adhesion and Sealing in Canine Dura Mater In Vitro A premix formed as in Example 13 was applied to a sample of canine dura mater bathed in saline at 37° C. The sealant formed a hard and durable substance within about 90 to 120 seconds of injection. The sample of dura mater was picked up with forceps and gentle pressure was applied to the edges. There was no tearing of the tissue seam.

We claim:

1. A biocompatible, biodegradable composition for use in sealing a biological tissue of a living mammal, the composition comprising a hydrogel, the hydrogel being produced by mixing a first solution comprising an acrylated chitosan with a second solution comprising oxidized dextran to produce a mixture comprising from about 1% to about 10% by weight of the acrylated chitosan that forms the hydrogel, wherein the acrylated chitosan has a degree of substitution of a chitosan backbone with acrylate groups in the range of from about 0.25 to about 0.5, and wherein the mixture, when applied to a biological tissue in need of sealing, forms a hydrogel within a minute after mixing thereby sealing the biological tissue.

2. The composition of claim 1 wherein the hydrogel is adapted to adhere to biological tissue of a living mammal, to adhesively seal the tissue.

3. The composition of claim 1 wherein the living mammal is a living human being.

4. The composition of claim 1 further comprising a dye material or a radio-opaque material.

5. The composition of claim 1 further comprising a therapeutic or protective agent.

6. The composition of claim 5, wherein the therapeutic or protective agent comprises an antimicrobial agent.

7. The composition of claim 5 wherein the therapeutic or protective agent comprises a peptide or a protein, a growth factor, or a bone morphogenic factor.

8. The composition of claim 5, wherein the therapeutic or protective agent comprises a bone powder or a bone substitute.

9. The composition of claim 5, wherein the therapeutic or protective agent comprises an anti-inflammatory agent.

10. The composition of claim 5, wherein the therapeutic or protective agent comprises an anti-cancer agent.

11. The composition of claim 5, wherein the therapeutic or protective agent comprises a radioactive material.

12. The composition of claim 1 wherein the acrylated chitosan concentration is about 3% to about 7% by weight.

13. The composition of claim 1, wherein the mixture comprises about 5% by weight of the acrylated chitosan.

14. The composition of claim 1, wherein the first solution comprises from about 1% to about 10% acrylated chitosan.

15. The composition of claim 1, wherein the degree of substitution is in the range from about 0.25 to about 0.45.

16. The composition of claim 1, wherein the degree of substitution is about 0.5.

* * * * *